(12) United States Patent
Boudoin et al.

(10) Patent No.: US 9,629,809 B2
(45) Date of Patent: *Apr. 25, 2017

(54) HIGH CONTENT SODIUM IBUPROFEN GRANULES, THEIR PREPARATION AND THEIR USE IN PREPARING NON-EFFERVESCENT SOLID DOSAGE FORMS

(71) Applicant: SI GROUP, INC., Schenectady, NY (US)

(72) Inventors: Latria N. Boudoin, Gonzales, LA (US); Gregory H. Lambeth, Baton Rouge, LA (US); Eric W. Llimatta, Baton Rouge, LA (US); Patrick C. Hu, Baton Rouge, LA (US)

(73) Assignee: SI GROUP, INC., Schenectady, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/714,768

(22) Filed: Dec. 14, 2012

(65) Prior Publication Data
US 2013/0136793 A1    May 30, 2013

Related U.S. Application Data

(63) Continuation-in-part of application No. 13/054,369, filed as application No. PCT/US2009/050405 on Jul. 13, 2009.

(60) Provisional application No. 61/082,445, filed on Jul. 21, 2008.

(51) Int. Cl.
A61K 9/20    (2006.01)

(52) U.S. Cl.
CPC .......... *A61K 9/2095* (2013.01); *A61K 9/2009* (2013.01); *A61K 9/2027* (2013.01); *A61K 9/2054* (2013.01)

(58) Field of Classification Search
None
See application file for complete search history.

(56) References Cited

U.S. PATENT DOCUMENTS

| | | | |
|---|---|---|---|
| 3,557,280 A | 1/1971 | Weber et al. | |
| 4,564,697 A | 1/1986 | Sutker | |
| 4,690,823 A | 9/1987 | Lohner et al. | |
| 4,859,704 A | 8/1989 | Haas | |
| 4,861,797 A | 8/1989 | Haas | |
| 5,071,643 A | 12/1991 | Yu et al. | |
| 5,104,648 A | 4/1992 | Denton et al. | |
| 5,360,615 A | 11/1994 | Yu et al. | |
| 5,445,827 A | 8/1995 | Fritsch et al. | |
| 5,456,925 A | 10/1995 | Smith et al. | |
| 5,912,011 A | 6/1999 | Makino et al. | |
| 6,322,816 B1 | 11/2001 | Zeidler et al. | |
| 6,387,400 B1 | 5/2002 | Tindal et al. | |
| 6,582,727 B2 | 6/2003 | Tanner et al. | |
| 2002/0034540 A1* | 3/2002 | Price | 424/464 |
| 2003/0049319 A1* | 3/2003 | Sriwongjanya et al. | 424/469 |
| 2004/0102522 A1 | 5/2004 | Gruber et al. | |
| 2005/0137262 A1 | 6/2005 | Hu et al. | |
| 2007/0043096 A1 | 2/2007 | Tidmarsh et al. | |
| 2008/0020042 A1 | 1/2008 | Gruber et al. | |

FOREIGN PATENT DOCUMENTS

| | | |
|---|---|---|
| EP | 0290168 A1 | 11/1988 |
| EP | 1800667 A1 | 6/2007 |
| WO | 94/14423 A1 | 7/1994 |
| WO | 97/30699 A2 | 8/1997 |
| WO | 9904765 A2 | 2/1999 |
| WO | 02/17855 A1 | 3/2002 |
| WO | 00/06125 A1 | 4/2004 |
| WO | 2004/035024 A1 | 4/2004 |
| WO | 2006/100281 A2 | 9/2006 |
| WO | 2010011522 A1 | 1/2010 |

OTHER PUBLICATIONS

Roberts et al. (Journal of Pharmacy and Pharmacology (55; 1223-1228 (2003)).*
RJ Roberts et al. (J. Pharm. Pharmacol. 1985, 37:377-384).*
Miwa et al. (International Journal of Pharmaceutics 195 (2000) 81-92).*
"A Product Guide Performance Enhancing Products for Pharmaceuticals" International Specialty Products, Copyright 2005; (20 pages).
Roberts, M., et al., "Effect of lubricant type and concentration on the punch tip adherence of model ibuprofen formulations", Journal of Pharmacy and Pharmacology, 2004, vol. 56, pp. 299-305.
Roberts, M., et al., "Effects of surface roughness and chrome plating of punch tips on the sticking tendencies of model ibuprofen formulations", Journal of Pharmacy and Pharmacology, 2003, vol. 55, pp. 1223-1228.
M. Roberts et al.; "Effect of Punch Surface Material on the Sticking Tendencies of Model Ibuprofen Formulations"; Journal of Pharmacy and Pharmacology; John Wiley & Sons Ltd. London, GB; vol. 55; Sep. 1, 2003; p. 76.
T. Uchimoto et al.; "Newly Developed Surface Modification Punches Treated With Alloying Techniques Reduce Sticking During the Manufacture of Ibuprofen Tablets"; International Journal of Pharmaceutics; vol. 441; 2013; pp. 128-134.
Website http://www.sizes.com/units/kilopond.htm; "What is a Kilopond?"; visited Dec. 23, 2013; 2 pages.
Website http://www.convertunits.com/info/kilopond; "Measurement Unit Conversion: Kilopond"; visited Dec. 23, 2013; 2 pages.

* cited by examiner

*Primary Examiner* — David J Blanchard
*Assistant Examiner* — Garen Gotfredson
(74) *Attorney, Agent, or Firm* — Jeffrey N. Townes; LeClairRyan

(57) ABSTRACT

Disclosed is a method for the preparation of easily-swallowed, reliably-dosed, aesthetically-improved tablets of sodium ibuprofen dihydrate, the method comprising the formation of the tablets with punches or presses comprising contact surfaces which are chrome or chrome-plated.

12 Claims, 17 Drawing Sheets

HIGH CONTENT SODIUM IBUPROFEN GRANULES, THEIR PREPARATION AND THEIR USE IN PREPARING NON-EFFERVESCENT SOLID DOSAGE FORMS

REFERENCE TO RELATED APPLICATIONS

This application is a CIP of U.S. application Ser. No. 13/054,369, filed Jan. 14, 2011, which is the National Stage of International Patent Application PCT/US2009/050405, filed on Jul. 13, 2009, which application claims priority from U.S. Application No. 61/082,445, filed Jul. 21, 2008.

TECHNICAL FIELD

This invention relates to high content granules of ibuprofen medicaments made from ibuprofen sodium salt dihydrate, to process technology for producing such granules, and to uses of such granules in preparing non-effervescent solid dosage forms for oral administration.

BACKGROUND

Sodium ibuprofen is an effective pain killer, and one of the advantages associated with it is the fact that it is easily absorbed through the lining of the stomach and can thus easily be taken in oral doses. According to the published literature, solid dosage forms made from sodium ibuprofen are superior in pharmaceutical kinetics (i.e., they enter and peak in the blood stream more rapidly than other solid dosage forms of ibuprofen). In fact, it is thought that sodium ibuprofen may be more effective in smaller amounts than its hydrogen substituted analog, ibuprofen, due to this ease of absorption.

Sodium ibuprofen is easily prepared as a powder. However, despite intensive research in the field, it remains difficult to prepare solid dosage forms from sodium ibuprofen using conventional approaches. One of the difficulties is that sodium ibuprofen dihydrate has poor flowability characteristics and thus tends to cake readily even when blended with conventional anti-caking agents such as colloidal silica or talc. The poor flow characteristics of sodium ibuprofen dihydrate, even though formulated with flow improvers, can result in erratic weight variations in the solid dosage forms such as tablets and caplets being produced.

Furthermore, sodium ibuprofen is unpalatable, having a taste that is difficult to mask; and when it is compressed into tablets, such tablets resist disintegration into the component powder, once swallowed, until reaching the stomach. Therefore, such tablets must be small enough such that they can easily transit as a whole down the esophagus.

A primary challenge in formulating sodium ibuprofen for easy dosing is the strong tendency for it to stick to the punch used to compress it into tablets, forming a film on the punch surface. It has been found that despite the use of lubricants, formulations high in sodium ibuprofen, including many of those of the present invention, are prone to sticking to punch surfaces. This film coating that is formed on the punch surface is undesirable from several standpoints. From an aesthetic standpoint, the coating on the punch reduces the "shine" of the tablets formed on that punch. From a practical perspective, the coating on the punch surface results in what is known as sticking, picking, and capping. A further disadvantage is that the punches must be cleaned of the accumulated sodium ibuprofen formulation or the aesthetic and dosage discrepancy can increase with time. However, cleaning the punch generally requires that the tableting operation temporarily be shut down, resulting in equipment downtime which inevitably increases the cost per unit.

One technique for reducing such sticking, is to reduce the proportion of sodium ibuprofen in the tablet, while maintaining the dosage amount at the same level. However, doing so can lead to tablets that are unacceptably large because in order to get the same amount of ibuprofen in a single tablet, the tablet must be increased in size in order to accommodate increased amounts of inert excipient.

While ibuprofen can be tableted, without sticking, with a wide variety of punching surfaces at a wide variety of tablet concentrations and dosages, sodium ibuprofen formulations have been observed to stick to most punch surfaces. In particular, formulations that are sufficiently high in active to give tablets of effective dose and easily swallowed size, have been observed to stick to some degree to nearly all types of punch surfaces.

Chemical differences between ibuprofen and its sodium salt analog are generally invoked by those of skill in the art to explain the difference in sticking properties. Ibuprofen is a racemic compound—methods of preparation generally give two enantiomers, and a single unit cell crystal of crystalline ibuprofen will contain one molecule of each enantiomer. However, sodium ibuprofen is a racemic conglomerate, i.e., it is generally characterized by an equal molar physical mixture of the individual enantiomeric crystals, such that only one enantiomer is present in each crystal and in each unit cell of the crystal lattice.

In the presence of water and some common excipients, the racemic conglomerate structural arrangement is distorted during wet granulation. As a result of the structure distortion, the heat of phase transition, which is normally at about 100° C., is greatly reduced leading to fragile crystals and structurally weak granules. Without desiring to be bound by theory, it is believed that the coating of the punch surface with sodium ibuprofen during tablet formation may occur due to a weak crystal structure caused by the above-mentioned crystal structure distortion a result of the changes in crystals. Thus, it has been thought by those of skill in the art that the propensity of sodium ibuprofen to stick to surfaces that ibuprofen did not stick to is a consequence of the chemical differences between the two compounds.

The above-described propensity for sticking, combined with the higher molecular weight of sodium ibuprofen dihydrate (264 g/mol) with respect to ibuprofen (which means that oral dose tablets must contain a greater wt % active than would be required of tablets of ibuprofen 206 g/mol)), has contributed to the under use of sodium ibuprofen despite its therapeutic advantages.

It would therefore be of considerable advantage if a way could be provided for forming sodium ibuprofen compositions capable of being more readily converted into solid dosage form such as tablets or caplets using conventional rotary press tableting equipment without encountering the various difficulties referred to above. It would also be of considerable advantage if a way could be provided for producing highly flowable granules from sodium ibuprofen dihydrate so that the dosage level of hard shell capsules filled with the granules can be kept more uniform. Furthermore, there exists a need for a tableting method, which produces acceptably-sized, reliably-dosed and aesthetically-acceptable sodium ibuprofen tablets.

This invention addresses all of the foregoing needs in an effective manner.

BRIEF NON-LIMITING SUMMARY OF THE INVENTION

Pursuant to this invention, it has been found that granules formed from racemic sodium ibuprofen dihydrate (a.k.a. sodium 2-(4-isobutylphenyl)propionate dihydrate, and hereinafter referred to more simply as sodium ibuprofen dihydrate), sodium carbonate, and polyvinylpyrrolidone (a.k.a. 2-pyrrolidone, 1-ethenyl-, homopolymer) by a wet granulation process has very desirable properties and the granules, when properly formulated, have flowability characteristics such that they can be effectively utilized in conventional rotary press tableting equipment without encountering the various difficulties referred to above. Moreover, it has been found that in the granulation operation and in the rotary press tableting operation, the advantageous results made possible by this invention can be achieved even though the amount of the sodium carbonate in the granules is only 3 wt % or less. Indeed, it has been found possible to produce excellent tablets from granules of this invention in which the granules contained only 2 wt % of sodium carbonate.

Furthermore, it has been found that the compositions of the present invention can be used in conjunction with tablet punches and presses having chrome-plated surfaces to produce aesthetic, reliably-dosed, easily-swallowed tablets. It has been found that by using a chrome-plated punch, it is possible for sodium ibuprofen formulations, comprising a sufficiently high concentration of sodium ibuprofen to be formed into tablets of a size that can be easily swallowed, to be punched into tablets with little or no tendency to stick to the surfaces of the punch. Remarkably, it has also been found that while the addition of a fatty acid wax compound, such as, for example stearic acid, is beneficial at reducing sticking of ibuprofen formulations to press surfaces, the method of the present invention can be used with formulations containing little or no wax to prepare aesthetically acceptable sodium ibuprofen dihydrate tablets having extremely high active content, as high as 90 wt %, 95 wt % or even higher.

By aesthetically-acceptable, it is meant that punch product, such as a tablet or caplet, is essentially free of any visible capping, picking or sticking of press or punch origin.

The fact that such extremely small amounts of sodium carbonate are effective in the formation of the granules and resultant tablets formed therefrom is also advantageous in connection with tablets consumed by more elderly persons. As is well known, as an individual ages, the acidity in the digestive tract tends to decrease, and thus such low levels of sodium carbonate in the tablets of this invention do not overly upset the digestive process in such individuals.

In one of its process embodiments, this invention provides:

A) A process for forming tables of sodium ibuprofen dihydrate, said process comprising forming tablets in a press comprising chrome contact surfaces, from granules of sodium ibuprofen dihydrate, the granules having been formed by a process comprising the steps of:

bringing together in a high shear granulator components comprised of (i) at least 80 parts by weight on a dry basis of sodium ibuprofen dihydrate, (ii) 1 to 4 parts by weight on a dry basis of sodium carbonate, (iii) 1 to 15 parts by weight on a dry basis of non-crosslinked polyvinylpyrrolidone, and (iv) 8 to 12 parts by weight of water based on the total weight of (i), (ii), (iii), and (iv) to form a wet mixture;

granulating said wet mixture in said high shear granulator to form wet granules;

drying wet granules to form dried granules having a moisture content in the range of about 11 to 15 wt %, and preferably in the range of about 12 to about 15 wt %, as determinable by measurement of weight loss at 110° C.; and removing by sieving dried granules having a particle size greater than 16 mesh.

Also provided are such processes wherein the main compression force is in the range of 10 to 20 kilonewtons; wherein the main compression is in the range of about 12 to about 16 kilonewtons; wherein the precompression force in the range of about 0.8 to about 1.0 kilonewtons; wherein the contact surfaces of the punch are chrome-plated; wherein the contact surfaces of the punch are chrome; wherein the punch speed is in the range of about 5 to about 20 RPM; wherein the press comprises a 10-station rotary press comprising chrome contact surfaces; wherein the main compression is in the range of about 12 to about 16 kilonewtons, and the press comprises a 10-station rotary press comprising chrome or chrome-plated contact surfaces; and wherein said granulating takes place in a high shear granulator. Also provided are tablets formed by such processes, including standard 400 mg as active round tablets.

Among the preferred process embodiments of this invention is the following:

B) A process as in A) above wherein the granulation of said wet mixture in said high shear granulator is conducted for a period of time such that after drying said wet mixture, the dried granules exhibit during differential scanning calorimetry a phase transition peaking in the range of about 100° C. to about 102° C., and wherein the size of the DSC peak, which peak corresponds to solids-to-solids phase transition, is at least about 150 joules per gram.

Among its composition embodiments, this invention provides:

C) A highly dispersible, free-flowing granule composition having a high content of sodium ibuprofen dihydrate, which composition is formed from components in powder form, said components comprising (i) 80 to 98 parts by weight of sodium ibuprofen dihydrate on a dry basis, (ii) 1 to 4 parts by weight of anhydrous sodium carbonate on a dry basis, and (iii) 1 to 15 parts by weight of non-crosslinked polyvinylpyrrolidone on a dry basis.

D) A sodium ibuprofen dihydrate formulation adapted for preparation of solid dosage forms using a rotary press, which formulation is formed from components which comprise:

about 40 to about 100 wt % of a granule composition as in C) above;

0 to about 25 wt % of microcrystalline cellulose, calcium hydrogen phosphate, or both;

0 to about 8 wt % of crospovidone or sodium croscarmellose;

0 to about 0.5 wt % of colloidal silica;

0 to about 10 wt % starch; and 0 to about 2 wt % stearic acid, magnesium stearate, or both.

Among preferred composition embodiments of this invention is the following:

E) A formulation as in D) above wherein said formulation exhibits during differential scanning calorimetry a phase transition peaking in the range of about 100° C. to about 102° C., and wherein the size of the DSC peak, which peak corresponds to solids-to-solids phase transition, is at least about 150 joules per gram.

Other embodiments, features, and advantages of this invention will become still further apparent from the ensuing description, accompanying drawings, and appended claims.

FURTHER DETAILED DESCRIPTION OF THIS INVENTION

Principal Components

Figure 1:
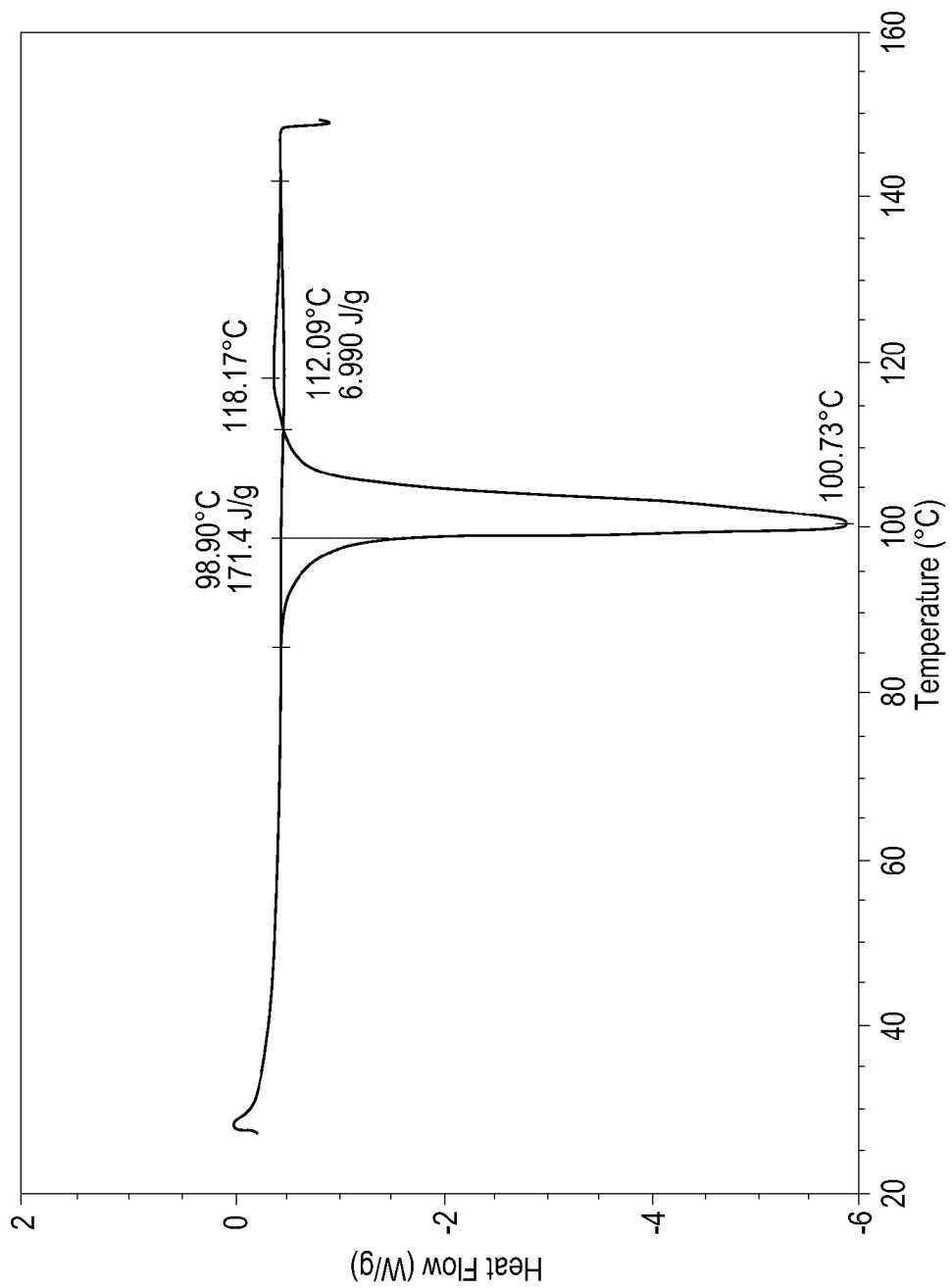
FIG. 1 is a differential scanning calorimetry curve of the granules of this invention produced in Example 11.
Figure 2:
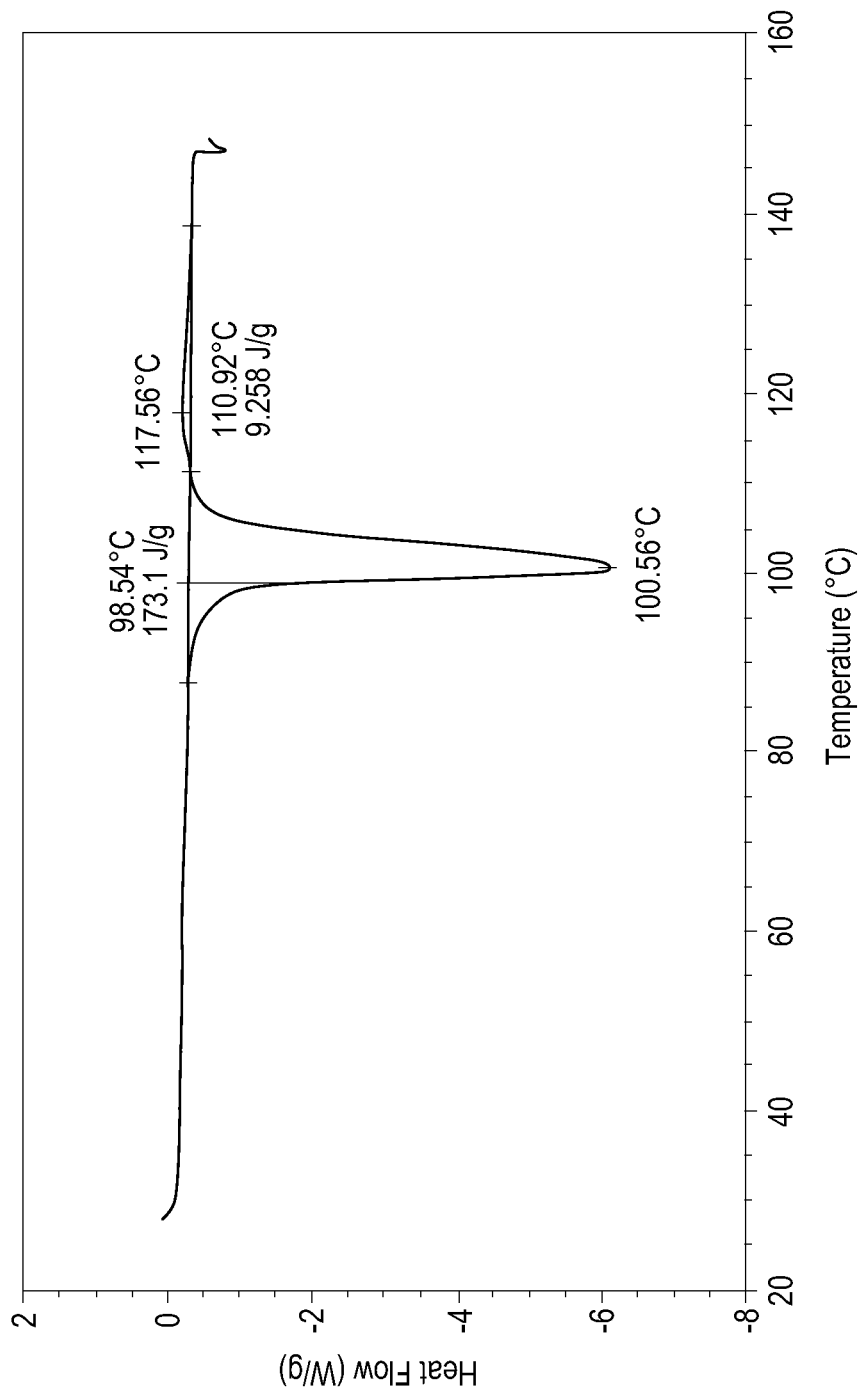
FIG. 2 is a differential scanning calorimetry curve of the granules of this invention produced in Example 12.
Figure 3:
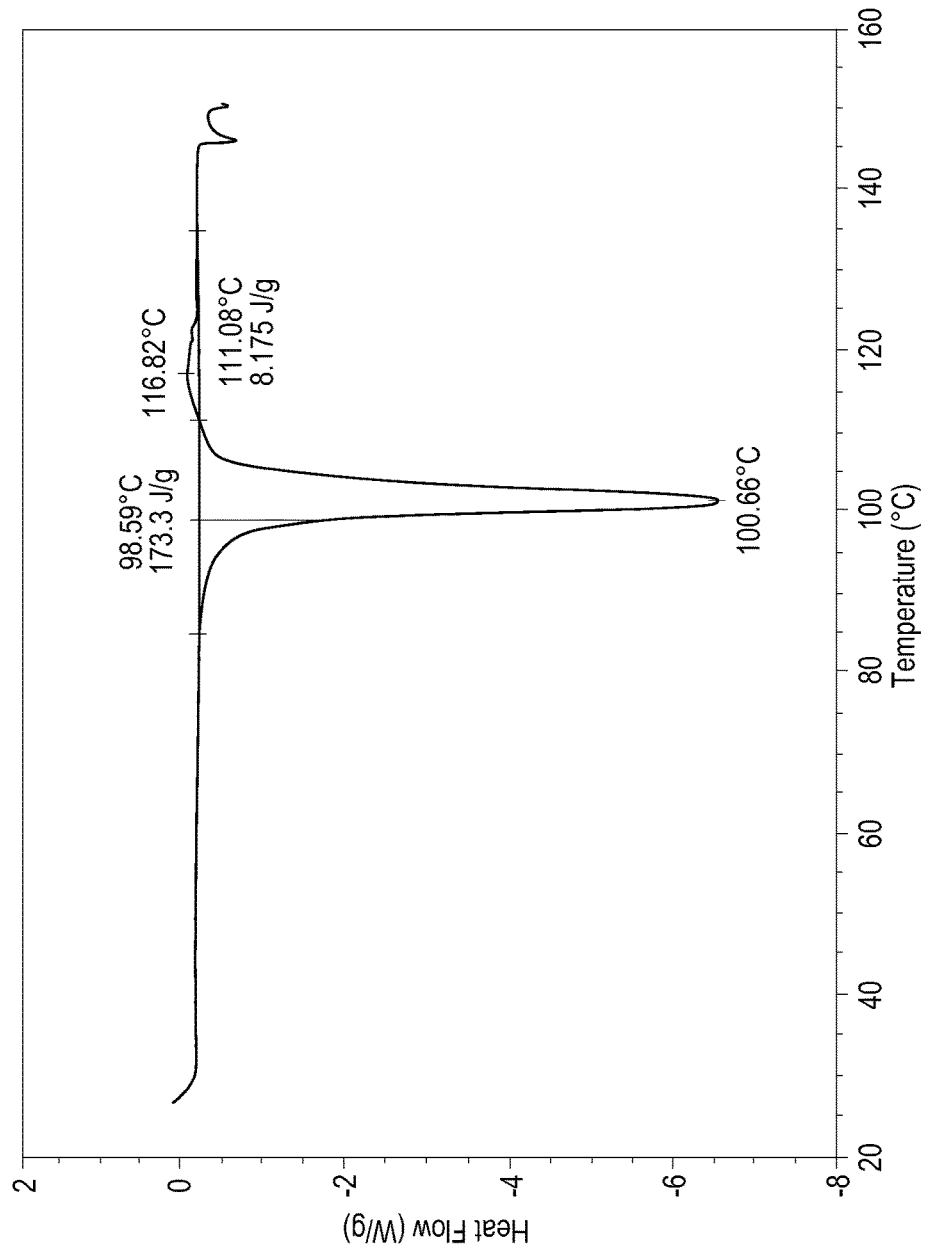
FIG. 3 is a differential scanning calorimetry curve of the granules of this invention produced in Example 13.
Figure 4:
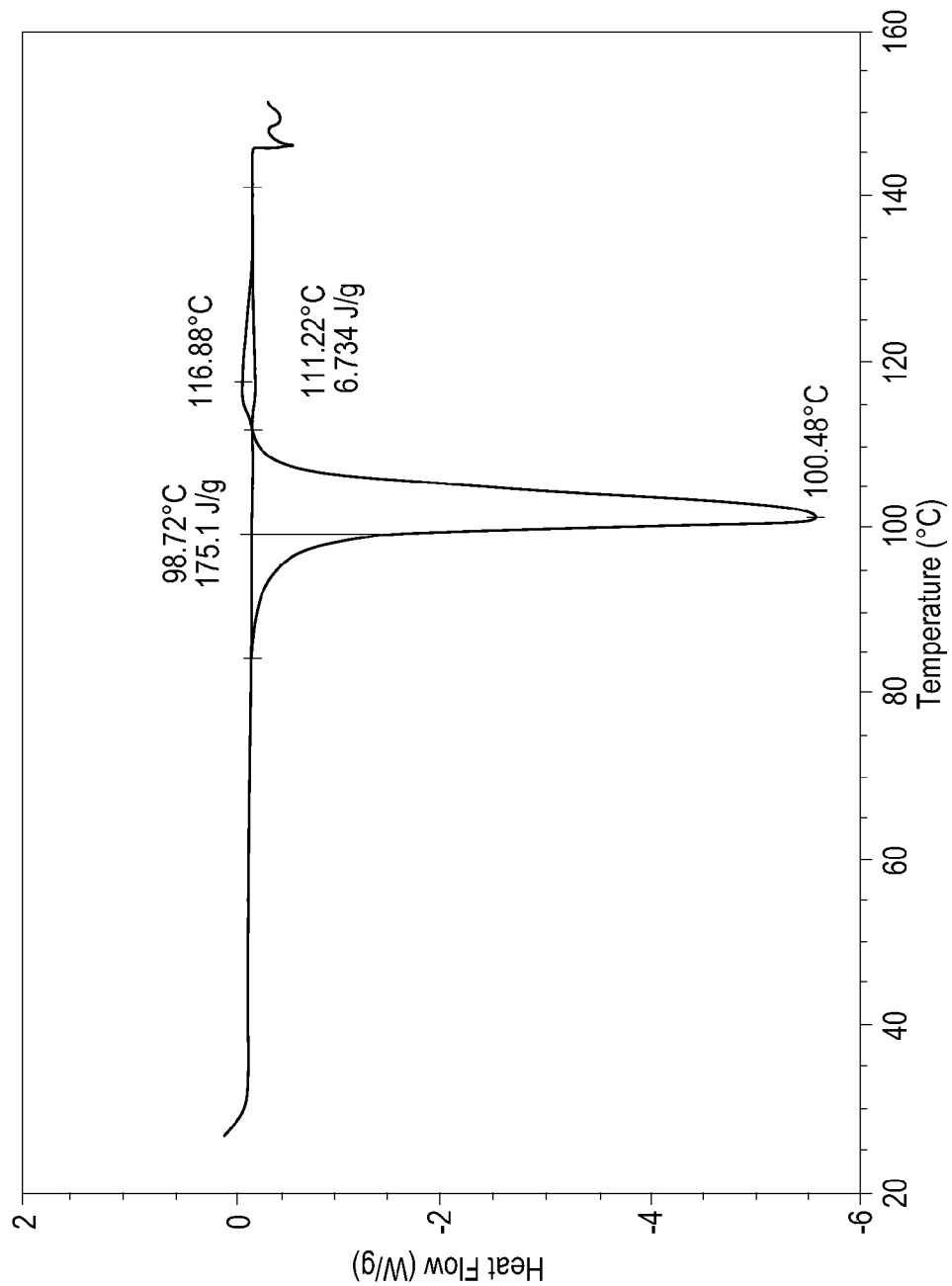
FIG. 4 is a differential scanning calorimetry curve of the granules of this invention produced in Example 14.
Figure 5:
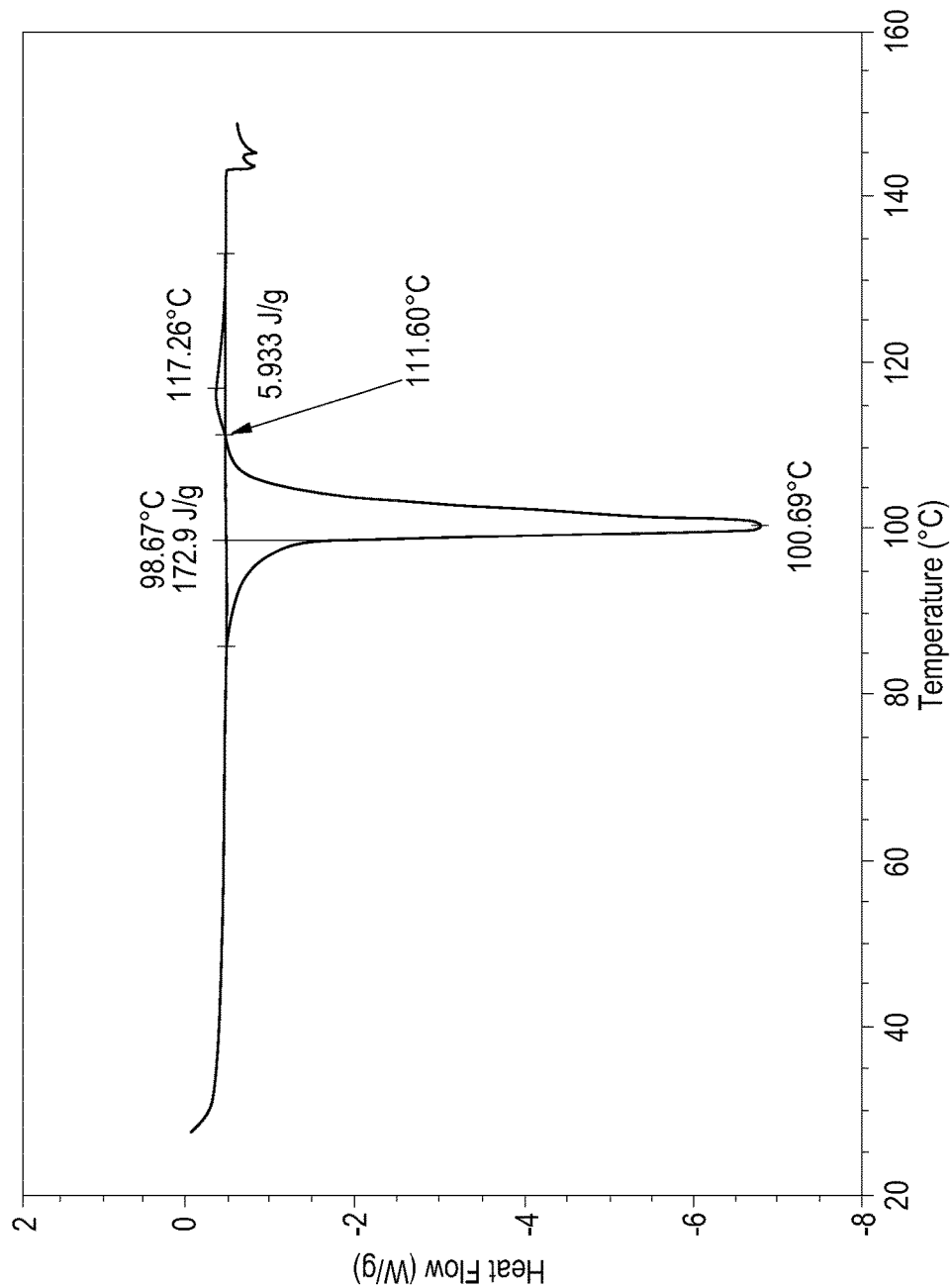
FIG. 5 is a differential scanning calorimetry curve of granules of this invention produced in Example 15 sampled with a drier inlet temperature set at 70° C., and when the drying temperature of the granules reached 35° C.
Figure 6:
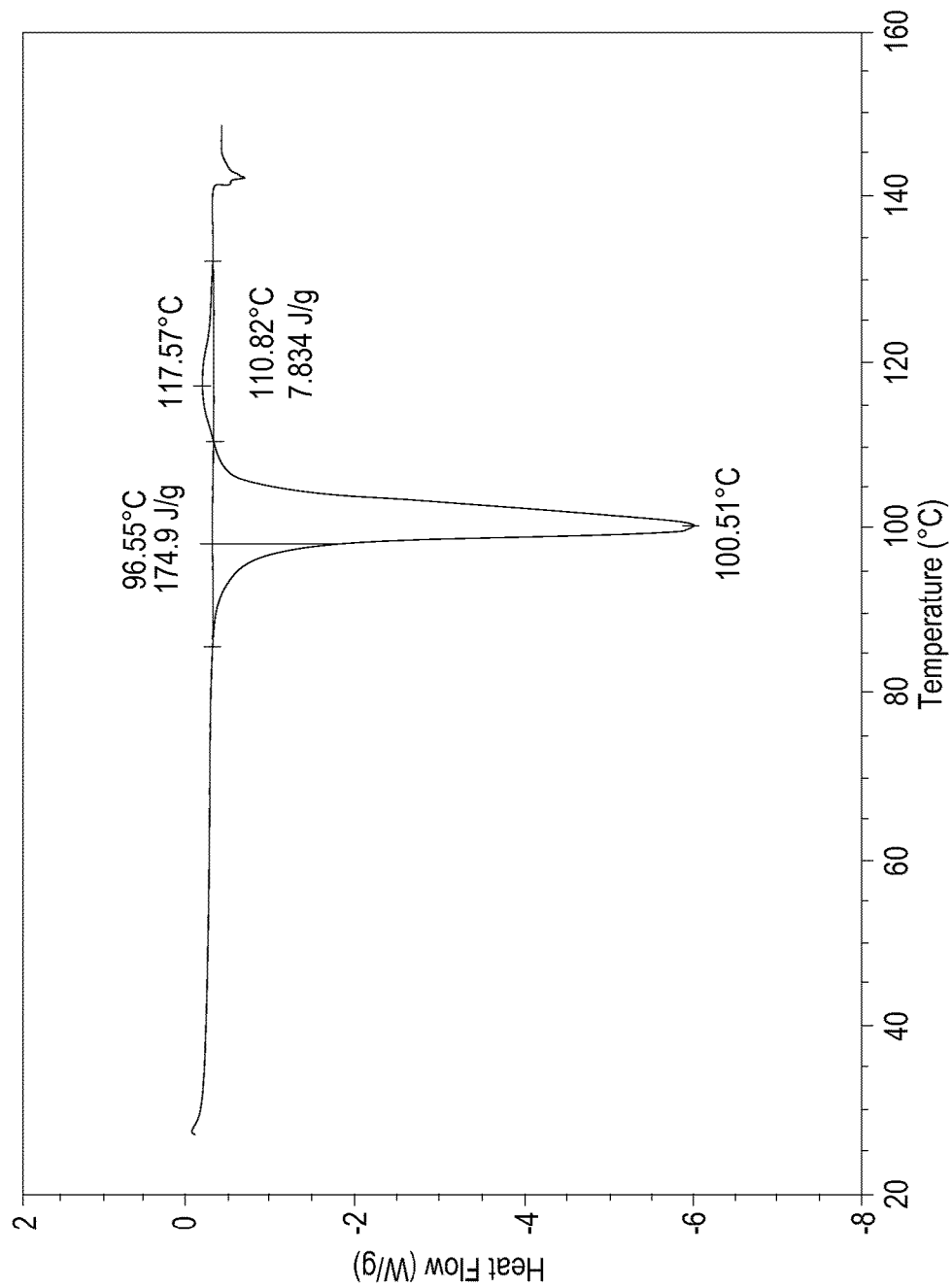
FIG. 6 is a differential scanning calorimetry curve of granules of this invention produced in Example 15 sampled with a drier inlet temperature set at 70° C., and when the drying temperature of the granules reached 40° C.
Figure 7:
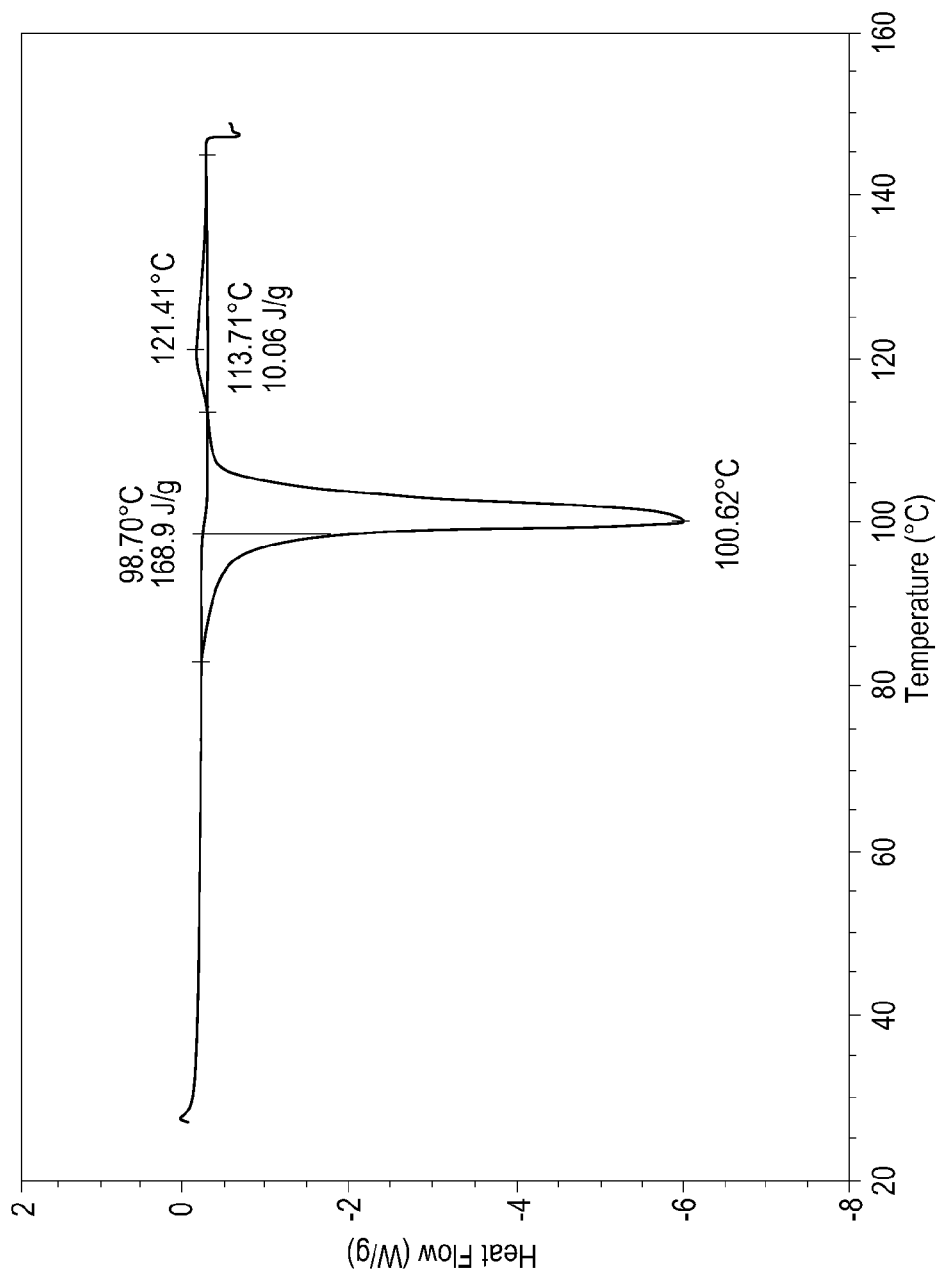
FIG. 7 is a differential scanning calorimetry curve of granules of this invention produced in Example 15 sampled with a drier inlet temperature set at 70° C., and when the drying temperature of the granules reached 45° C.

As noted above, there are three principal components in the granules of this invention and in the solid dosage forms of this invention such as tablets, caplets, and hard shell capsules. These are sodium ibuprofen dihydrate, sodium carbonate and polyvinylpyrrolidone. Each of these components is well-known in the art and methods for the preparation of these respective materials are also well-known and are reported in the literature. All such components should be of NF, USP, or multicompendial grade. In other words, they should be of pharmaceutically acceptable purity, grade, and/or quality.

Preparation of Granules of this Invention

To prepare the granules of this invention, the above three principal components are mixed in appropriate proportions relative to each other while wet with water in a high shear granulator. In practice, it is desirable to form a solution of the polyvinylpyrrolidone in water prior to forming the overall mixture of the three components. This will provide a more uniform distribution of polyvinylpyrrolidone in the granules. After blending and granulation in the high sheer granulator, water is removed from the wet granules by a conventional drying procedure such as pan drying in an oven or by fluidized bed drying. Typically, the drying is effected at a temperature of up to about 100° C. Preferably, oven temperatures for drying of the granules is in the range of about 60 to about 70° C. In the case of a fluidized bed dryer, the inlet temperature is also preferably in the range of about 60 to about 70° C. In a particularly preferred drying operation, the temperature of the outlet air is monitored so that the drying is terminated when the outlet air temperature reaches about 40° C. In this way the total moisture content of the granules is in the preferred range of about 12 to about 15, and more preferably is around 13.5 wt %, which is about the amount of hydrate water in sodium ibuprofen dihydrate. The dried product is then sieved to remove oversized material (e.g., greater than 16 mesh). Such oversized material is typically milled and recycled to the granulation operation.

In greater detail, it is preferred to charge the sodium ibuprofen dihydrate into the high shear granulator followed by a preformed solution of polyvinylpyrrolidone in water. After thorough blending of these components the requisite amount of sodium carbonate is then added and the mixture is subjected to additional high shear granulation. The granulation is conducted at a temperature in the range of about 15 to about 35° C., using cooling if necessary to remove excess heat generated during granulation. The rate of shear of the chopper in the high shear granulator prior to addition of the sodium carbonate is typically in the range of about 1000 to about 2000 rpm for a period in the range of about 3 to about 6 minutes. The chopper rate is then reduced to a low shear rate of about 200 to about 500 rpm for an additional period of about 3 to about 6 minutes. After the addition of the sodium carbonate, this same two stage operation of the chopper is repeated (i.e., ca. 1000 to ca. 2000 rpm for ca. 3 to ca. 6 minutes and then ca. 200 to ca. 500 rpm for ca. 3 to ca. 6 minutes).

Depending upon the design of the high shear granulator, the apparatus may contain another mechanism for effecting motion of the mixture in the granulator, which mechanism is known as a paddle. The rate at which the paddle is operated is of lesser importance and thus can be varied. When using a 160 liter, Fluid Air Pharmx High Shear Granulator, Model PX150, it was found convenient to operate the paddle in a two stage manner in which during the first stage the paddle was operated at 100 rpm and in the second stage at 30 rpm. These stages coincided with the two stage operation of the chopper.

The sodium carbonate used in forming the granules should be of NF or USP grade and initially may be hydrated, but preferably is in the form of an anhydrous powder. Polyvinylpyrrolidone of pharmaceutically acceptable grade is available in various forms which may be used in the practice of this invention. However, it is preferred to utilize polyvinylpyrrolidone with a K value in the range of 30 to 120, with a K value of 90 being more preferred. The sodium ibuprofen dihydrate is a racemic mixture of pharmaceutically acceptable grade and preferably is used in powder form.

The amount of sodium carbonate used in forming the granules is typically in the range of about 1 to 4% by weight of the total mixture. Preferably the amount is in the range of about 2 to about 3% by weight of the total mixture. In forming the granules, the amount of polyvinylpyrrolidone is typically in the range of about 1 to about 10% by weight of the total mixture. Preferably, the amount of polyvinylpyrrolidone is in the range of about 2 to about 4 by weight of the total mixture. Preferably, the balance to 100% by weight of the total mixture is composed of sodium ibuprofen dihydrate. If desired, other conventional pharmaceutically-acceptable excipients can be used, provided they do not adversely interact with any of the three principal components or otherwise interfere with the preparation of the granules or solid dosage forms produced therefrom. However, inclusion of such excipients in the granules is not advisable since such usage would reduce the concentration of the sodium ibuprofen dihydrate in the granules and result in increased production costs and record keeping.

The water used is also of sufficient purity to meet regulatory requirements. The amount of water used in forming the granules is typically in the range of about 5 to about 15 wt % of the total weight of the wet mixture of components. Preferably, the amount of water used for granule formation is in the range of about 8 to 12 wt % of the total weight of the wet mixture of components. If too little water is used, insufficient granulation will occur. On the other hand, if too much water is used, the mixture will have the consistency of a bakery dough. In either case, after drying, the product will not have a desirable average (mean) particle size. In this connection, the average particle size of the dry granules is typically in the range of about 150 to about 600 microns, and preferably is in the range of about 200 to about 300 microns.

Especially preferred granules of this invention in wet form are prepared from the following components in the amounts specified: sodium ibuprofen dihydrate, 85.95 wt %; non-crosslinked polyvinylpyrrolidone (especially K-90), 2.25 wt %; anhydrous sodium carbonate powder, 1.80 wt %; purified water, 10 wt %. Especially preferred granules of this invention in dry form have the following composition: 95.50 wt % as sodium ibuprofen dihydrate; 2.50 wt % of polyvinylpyrrolidone (especially K-90); and 2.00 wt % as anhydrous sodium carbonate.

Preferred Granules and Granule Formulations

As indicated above, this invention provides in preferred embodiments granules and granules formulations which are characterized by exhibiting during differential scanning calorimetry a phase transition peaking in the range of about 100° C. to about 102° C., and wherein the size of the DSC peak, which peak corresponds to solids-to-solids phase transition, is at least about 150 joules per gram. The existence of this peaking ensures that the granules, when suitably formulated—as in the formulation designated E) above—will produce solid dosage forms having excellent processing characteristics in a rotary press and that will thereby produce solid dosage forms of high quality that will comply with present day regulatory requirements. There are various ways of ensuring that the granules and the resulting formulation will have the foregoing DSC thermal characteristics during differential scanning calorimetry (DSC). For example, if the granule samples do not exhibit such DSC thermal characteristics:

The granules can be heated at a temperature and for a period of time sufficient to achieve the foregoing DSC thermal characteristics. Suggested heating conditions include heating at about 30 to about 70° C. for a period of about 5 to about 50 minutes;

The time period during which wet granulation is conducted can be increased. In bench scale operations, this total period of wet granulation was found to be at least about 12 to 16 minutes. When the operation is conducted on a larger scale, the total period of wet granulation may differ at least somewhat from 12 to 16 minutes in order to achieve the desired DSC thermal characteristics, and thus a few pilot experiments should be conducted if necessary, in order to determine the appropriate time period for wet granulation when operating on a larger scale;

Avoid inclusion of components in the granulation processes when the granules are still wet will cause failure to achieve the foregoing DSC thermal characteristics. Components found detrimental in this respect are starch, sodium starch glycolate, and magnesium stearate. As will be seen from Examples presented hereinafter, once the granules have been dried, microcrystalline cellulose can be utilized as a component in formulations for use in producing solid dosage forms. Indeed, microcrystalline cellulose is a preferred component for use in such formulations.

Other embodiments, features, and advantages of this invention will become still further apparent from the ensuing description, accompanying drawings, and appended claims.

Unlike other sodium ibuprofen formulations, the formulations of the present invention can be used to easily form tablets having high doses of ibuprofen as well as being small enough to easily swallow, as well as aesthetically acceptable and reliably dosed. Such tablets are made possible by the use of chrome surfaces to contact the ibuprofen during tablet formation, for example, a punch having chrome or chrome-plated punch surfaces which are in contact with the active during at least the main compression stage of the tablet compression process. Without limiting this invention, punches that are known and used in the art, for example, rotary press punches (such as 10-station rotary press punches available from Globepharma, Inc.,), and the like, may be suitable for use in processes of this invention. If necessary, the punch surfaces can be altered from their purchased state by chrome-plating the surfaces after purchase. A distinction is made between surfaces, which are "chrome", and surfaces, which are "chrome-plated." The former is a chrome surface, which has not been laid by electroplating. Examples of the former include surfaces which are part of a solid chrome bulk, regardless of whether the bulk is a tablet formation cavity that is itself of chrome, or a "veneer" or a pressure applied layer of chrome. The latter applies to a layer of chrome, which is deposited, on an atomic scale, such as via electroplating chemical vapor deposition or the like. Both chrome and chrome-plated surfaces are included within the ambit of the present inventive method. In one embodiment the press comprises a GLOBEPHARMA 10-station rotary press comprising chrome contact surfaces.

It is expected that a wide variety of punch parameters (main compression force, initial compression force, punch speed, tablet size) can be used and the aesthetic advantages of the method will still be manifested. In more specific embodiments, the settings can include a main compression force of between about 8 and about 22 kilonewtons, with between about 10 and about 20 kilonewtons more preferable in order to minimize capping and occasional tablet breakage. In another preferred embodiment, the main compression is between about 12 and about 16 kilonewtons. The initial compression step is generally for the purpose of minimizing the air in the precompressed formulation prior to main compression. The variations in initial compression force are not expected to greatly affect the beneficial effects of the inventive method. In general, initial compression forces, which can be in the range of from 0.4 to 0.01 of the than the main compression force, are used, with wide variations not expected to greatly affect the aesthetic and consistent dosage advantages. In one preferred embodiment, the main compression is in the range of about 12 and about 16 kilonewtons, and the initial compression is in the range of about 0.8 to about 1.0 kilonewtons. It has been found that the ejection force does not greatly affect the lack of sticking to chrome punch surfaces, but in one embodiment, the ejection force is in the range of 0.1 to about 0.5 kilonewtons. The inventive method can be used in a wide variety of punch sizes, such as for ibuprofen round or caplets that contain 200, 400, 600, and 800 of active. In one embodiment the tablet size is a standard 400 mg active round size. Punch speed has little effect on the ability of the present method to exhibit little or no sticking to the surfaces of chrome presses. In general a punch RPM in the range of from about 5 to about 20 RPM can be conveniently used. It should be noted that optimum compression force, pre-compression force, ejection force and RPM punch setting ranges can vary from one tablet press to another. It may be necessary to establish set points for each tablet press individually. One of skill in the art will have the knowledge necessary to establish the set points in order to obtain the benefits of the invention, given the teachings of our specification.

Furthermore, it has also been found that while the addition of a fatty acid wax compound, such as, for example stearic acid, is beneficial at reducing sticking of ibuprofen formulations to press surfaces, the method of the present invention can be used with formulations containing no wax.

However, one or more lubricants can be included in the formulation. If a lubricant is used, it is preferred to use a wax-based lubricant, examples of which include stearic acid, magnesium stearate, calcium stearate, sodium lauryl sulfate, and the like, with stearic acid being preferred. However, non-wax-based lubricants such as fumed silica, talc, or other mineral lubricants can be used. While such lubricants are not essential, if a wax based lubricant is used, it is preferred to be used in amounts in the range of about 1 to about 1.5 wt % percent based upon the weight of the dry formulation. If, in addition to the wax-based lubricant or instead of the wax-based lubricant, a mineral or other non-wax lubricant is used, it is preferred that the lubricant be used in amounts in the range of 1 to 1.5 based upon the weight of the dry formulation.

It should be noted that the non-stick preparation of tablets can be carried out with granules which have been granulated in a variety of ways. Methods of granulation which can be used include, but are not limited to, low shear granulation, high shear granulation and fluidized-bed granulation, with high shear granulation preferred.

Thus, in one embodiment, the present invention comprises a process for forming tablets of sodium ibuprofen dihydrate, said process comprising forming tablets in a press comprising chrome contact surfaces, from granules of sodium ibuprofen dihydrate, the granules having been formed by a process comprising the steps of
bringing together in a high shear granulator components comprised of (i) at least 80 parts by weight on a dry basis of sodium ibuprofen dihydrate, (ii) 1 to 4 parts by weight on a dry basis of sodium carbonate, (iii) 1 to 15 parts by weight on a dry basis of non-crosslinked polyvinylpyrrolidone, and (iv) 8 to 12 parts by weight of water based on the total weight of (i), (ii), (iii), and (iv) to form a wet mixture;
granulating said wet mixture in said high shear granulator to form wet granules;
drying wet granules to form dried granules having a moisture content in the range of about 12.5 to 15 wt % as determinable by measurement of weight loss at 110° C.; and
removing by sieving dried granules having a particle size greater than 16 mesh.

In another embodiment, the invention further comprises the use of granules which are lubricant free in the inventive process. In further embodiments, the invention comprises a process in which the tablets produced by the inventive process above are lubricant-free. In another embodiment, the invention comprises tablets formed by the inventive process. In yet another embodiment, the tablets formed by the inventive process are lubricant-free.

The following Examples are presented for the purposes of illustration. They are not intended to limit the invention to only the details and materials set forth therein.

EXAMPLE 1

Preparation of Granules

Granules composed of 95.5 wt % of sodium ibuprofen hydrate, 2 wt % of sodium carbonate and 2.5 wt % of polyvinylpyrrolidone (Plasdone K-90, International Specialty Products Inc., Wayne, N.J.) were prepared by a wet granulation process of this invention. The process used involved dissolving the Plasdone K-90 in water, adding the solution to sodium ibuprofen dihydrate in a V-blender equipped with a high shear intensifier drive (MAXI-BLEND LAB V-BLENDER manufactured by GlobePharma, Inc., New Brunswick, N.J.), and forming the granule by operating the blender using high shear, adding sieved sodium carbonate powder to the wet mixture in the blender, mixing for another 5 minutes utilizing the intensifier drive. After discharging the blender content into a pan, the granules were dried in an oven maintained at 50° C. until all added water was removed. The product was then sieved through a stainless steel 16-mesh U.S.A. standard sieve.

EXAMPLE 2

Preparation of Tablets

EXAMPLE 2A

The granules formed as in Example 1 were used to prepare a fully formulated blend for tablet preparation using rotary press. In this operation, the granules were mixed with microcrystalline cellulose (MCC) and colloidal silica by means of dry blending. The formulation processed well in a 10-station rotary press and the resulting tablets showed good friability, dissolution, and disintegration. The final blend was composed of 75 wt % of sodium ibuprofen hydrate, 2.37 wt % of polyvinylpyrrolidone, 1.58 wt % of sodium carbonate, 20.95 wt % of microcrystalline cellulose, and 0.1 wt % of colloidal silica.

The characteristics of the high active-content granules formed as in Example 1 and the tablet formulation formed as in Example 2A are given in Table 1. The flowability index showed that both the granules and the fully formulated blends have good flow characteristics. In addition, the tablets met all desired performance criteria.

TABLE 1

|  | Granules | Tablet Formulation |
| --- | --- | --- |
| Flowability No. | 78.5 | 81.5 |
| Areated Bulk Density | 0.641 | 0.569 |
| Packed Bulk Density | 0.687 | 0.619 |
| Compressibility | 6.60% | 8.00% |
| Angle of Repose | 40.7° | 37.0° |
| Angle of Spatula | 45° | 44° |
| Uniformity | 6.3 | 4.4 |

EXAMPLE 2B

Granules formed as in Example 1 were used to prepare a fully formulated blend for tablet preparation using rotary press, as described in Example 2A, except that the granules were mixed with crospovidone by means of dry blending. The formulation processed well in a 10-station rotary press and the resulting tablets showed acceptable friability and good dissolution properties. The final blend was composed of 93.6 wt % of sodium ibuprofen hydrate, 2.45 wt % of polyvinylpyrrolidone, 1.96 wt % of sodium carbonate, and 2 wt % of crospovidone.

EXAMPLE 2C

Granules formed as in Example 1 were used to prepare a fully formulated blend for tablet preparation using rotary press, as described in Example 2A, except that the granules were mixed with Na croscarmellose by means of dry blending. The formulation flowed well into a 10-station rotary press and the resulting tablets showed acceptable friability and good dissolution properties The final blend was composed of 93.6 wt % of sodium ibuprofen hydrate, 2.45 wt % of polyvinylpyrrolidone, 1.96 wt % of sodium carbonate, and 2 wt % of Na croscarmellose.

EXAMPLES 3-10

In these Examples, runs were made using the wet granulation technique in a bench scale high shear granulator, Model PX1, 2-Liter Fluid Air High Shear Granulator. This apparatus includes an impeller and a chopper disposed in a bowl. The impeller rotates in a circular path within the bowl, the blend to be granulated within the bowl and the chopper breaks up large particles formed in the blend during processing. The granulator is operated by compressed air and, in operation, some compressed air enters the bowl and contributes to the formation of a blend having a consistency resembling marshmallow consistency, i.e., the blend is soft and of low density. Upon further blending, part of the trapped air is released. The blend has a wet appearance. The appearance of the resultant granules is significantly different from the granules processed in a twin-shell blender using the same formulation. The granules from a twin-shell blender appear much dryer than the granules produced in the present apparatus.

In a typical operation, after adding sodium ibuprofen dihydrate to the bowl, a lid is placed on the bowl, the chopper and impeller rates are set at 2500 and 300 RPM, respectively. Immediately after turning on the mixing, an aqueous solution of povidone K-90 is poured into the granulator through a hole in the lid. It typically takes about 100 seconds to transfer the liquid to the bowl through the small hole in the bowl cover. After povidone solution transfer, the high shear blending is continued for a preset time. Then the mixing rates of both chopper and impeller are reduced to about half of the original settings and this low shear mixing is continued for another few minutes. Anhydrous sodium carbonate powder (previously sieved through a 20-mesh screen) is then added to the bowl and the mixing continued for another high shear-low shear mixing cycle. The wet granules produced in run 1 were discharged into a beaker before adding to a fluid bed dryer. Dried materials collected in plastic bags show the presence of significant amount of granules of greater than 16 mesh.

The operations involved two stages. In the first stage, sodium ibuprofen dihydrate and polyvinylpyrrolidone (K-90 solution) were added to the granulator and mixed. In the second stage, finely divided anhydrous sodium carbonate was added to the granulator contents from the first stage, and the resultant mixture was processed into granules.

The conditions of wet granulation operation in the first stage of Examples 3-10 are summarized in Table 2. Table 3 summarizes the conditions of wet granulation operation used in the second stage. In Tables 2 and 3, the designation "CPR" designates "chopper", "IMP" designates "impeller", and "n/a" designates "not applicable".

TABLE 2

CONDITIONS USED IN STAGE 1 OPERATION

|  | De-lumping | | | PVP K-90 solution addition/mixing | | | Mixing | | |
| --- | --- | --- | --- | --- | --- | --- | --- | --- | --- |
| Ex. No. | CPR | IMP | Time | CPR | IMP | Time | CPR | IMP | Time |
| 3 | 2500 | 300 | 15 | 2500 | 300 | 95 | 2500 | 300 | 120 |
| 4 | 2500 | 300 | 180 | 2500 | 300 | 300 | 500 | 150 | 300 |
| 5 | n/a | n/a | 0 | 2500 | 300 | 90 | 1000 | 150 | 210 |
| 6 | n/a | n/a | 0 | 2500 | 300 | 110 | 1000 | 150 | 210 |
| 7 | n/a | n/a | 0 | 2500 | 300 | 205 | 1000 | 150 | 210 |
| 8 | n/a | n/a | 0 | 2500 | 300 | 180 | 1000 | 150 | 210 |
| 9 | n/a | n/a | 0 | 2500 | 300 | 225 | 1000 | 150 | 210 |
| 10 | n/a | n/a | 0 | 2500 | 300 | 93 | 1000 | 150 | 210 |

Units used for chopper & impeller are RPM and time is in seconds, unless otherwise specified.

TABLE 3

CONDITIONS USED IN STAGE 2 OPERATION

| Ex. No. | CPR | IMP | Mixing time | CPR | IMP | Mixing Time |
| --- | --- | --- | --- | --- | --- | --- |
| 3 | 2500 | 300 | 60 | 1000 | 150 | 0 |
| 4 | 0 | 0 | 480 | 1000 | 150 | 360 |
| 5 | 2500 | 300 | 90 | 1000 | 150 | 210 |
| 6 | 2500 | 300 | 90 | 1000 | 150 | 210 |
| 7 | 2500 | 300 | 90 | 1000 | 150 | 210 |
| 8 | 2500 | 300 | 90 | 1000 | 150 | 210 |
| 9 | 2500 | 300 | 90 | 1000 | 150 | 210 |
| 10 | 2500 | 300 | 90 | 1000 | 150 | 210 |

Units used for chopper & impeller are RPM and for time are seconds, unless otherwise specified.

In Example 4 de-lumping efficiency of the high shear chopper was measured by checking the presence of lumps in the granulator at various blending intervals. It was concluded that de-lumping of sodium ibuprofen dihydrate in its original particulate form is not efficient and de-lumping becomes significantly more efficient after the povidone solution is added. We found no detectable lumps after about 120 seconds at the high shear mixing cycle. After the granulator operation, the contents of the granulator bowl were transferred to a fluidized bed dryer pneumatically using a vacuum tube applied to the hole in the cover and with suction generated by the fluid bed dryer. The dried materials collected showed very little content of granules greater than 16-mesh in size. Because of these findings in Examples 5-10 the de-lumping steps were omitted and vacuum transfer to the fluidized bed dryer was employed.

Example 5 went smoothly and the granules produced looked good. It was decided then that we should check the robustness of the process. There are two aspects of process robustness. The first is the ability of the process to produce granules with the same quality on a consistent basis. The second aspect of process robustness is whether the process can be carried out, independently, with a skilled technician. Accordingly, a skilled technician carried out the operations of Examples 6-10.

In Example 6, in addition to the conditions summarized in Tables 1 and 2, the dryer parameters were documented. The data relating to the dryer operation are summarized in Table 4. In all cases, vacuum transfer to the fluidized bed dryer was used.

TABLE 4

SUMMARY OF DRYER OPERATION IN EXAMPLE 6

| Time, minutes | Air flow rate, SCFM | Inlet temp, ° C. | Outlet temp, ° C. | Product temp, ° C. |
|---|---|---|---|---|
| 0 | 8 | — | — | 14 |
| 1 | 9 | 24 | 37.8 | 14 |
| 8 | 8 | 58.3 | 39.7 | 20 |
| 12 | 8 | 74.2 | 45.7 | 32.8 |
| 15 | 8 | 68.9 | 40.7 | 40.7 |

Evaluations were made of the properties of the granules produced in Examples 4-10. In conducting these evaluations, all the granules from each run were individually sieved and the amounts of material retained on a 16-mesh screen were recorded. The sieved materials were then measured for particle size distribution using the light scattering method. Moisture contents of the granules was determined in two separate laboratories, independent of each other, using moisture balances at a set temperature of 110° C. The results of these evaluations are summarized in Table 5 in which "STDEV" denotes standard deviation and "RSTD" denotes relative standard deviation.

TABLE 5

EVALUATION OF GRANULES

| Ex. No. | >16-mesh, Size Fraction, wt % | Mean Particle Size, microns | Moisture, wt %, weight loss at 110° C., By Laboratory 1 | Moisture, wt %, weight loss at 110° C., By Laboratory 2 |
|---|---|---|---|---|
| 4 | 1.9 | 207 | 13.4 | 13.4 |
| 5 | 3.7 | 252 | 13.3 | 13.5 |
| 6 | 2.9 | 228 | 13.3 | 13.3 |
| 7 | 4.5 | 245 | 13.2 | 13.5 |
| 8 | 2.8 | 263 | 13.3 | 13.4 |
| 9 | 2.4 | 234 | 13.4 | 13.3 |
| 10 | 0.6 | 220 | 13.4 | 13.5 |

TABLE 5-continued

EVALUATION OF GRANULES

| Ex. No. | >16-mesh, Size Fraction, wt % | Mean Particle Size, microns | Moisture, wt %, weight loss at 110° C., By Laboratory 1 | Moisture, wt %, weight loss at 110° C., By Laboratory 2 |
|---|---|---|---|---|
| Average | 2.7 | 235 | 13.3 | 13.4 |
| STDEV | 1.3 | 19 | 0.1 | 0.1 |
| % RSTD | 47.31% | 8.22% | 0.60% | 0.61% |

Distribution of active contents in fractions of the granules was also evaluated. This evaluation involved separately sieving about 100 grams of granules from runs 2 and 8 through a stack of stainless steel sieves. Size fractions in (a) units of wt % and (b) active contents of fractions as determined by HPLC, reported as percentages of theoretical value, are given in Table 6, in which "µ" denotes micron. It can be seen from the results in Table 6 that there is a tendency for the higher active contents to be found in the smaller sized particles.

TABLE 6

WEIGHT AND ACTIVE CONTENTS OF SIEVED FRACTIONS OF DIFFERENT SIZES

| Sieves Opening | Run # 8 Sieve Retention | Run # 8 Theoretical Active content | Run # 2 Sieve Retention | Run # 2 Theoretical Active Content |
|---|---|---|---|---|
| 16 mesh (1180 µ) | 0.60% | 98.0% | 1.9% | 98.8% |
| 30 mesh (600 µ) | 0.33% | 79.2% | | |
| 40 mesh (425 µ) | 0.48% | 55.3% | | |
| 60 mesh (250 µ) | 15.53% | 94.2% | 17.0% | 96.8% |
| 80 mesh (180 µ) | 29.22% | 98.4% | 33.9% | 99.8% |
| 100 mesh (150 µ) | 23.97% | 99.3% | 26.5% | 102.1% |
| 200 mesh (75 µ) | 22.64% | 102.9% | 19.0% | 103.1% |
| pan (<75 µ) | 7.25% | 100.9% | 2.5% | 103.7% |

The evaluation of the granules indicates that from the standpoints of particle size distribution, active content in varying size fractions, and particle friability point of view, the process is quite robust.

Experiments were conducted in order to evaluate the performance of granules produced in some of the above Examples in tablet formation. Granules from Examples 9 and 10 in their original sealed bags were placed in a 50° C. oven for 20 hours and, after allowing them to cool to room temperature, these granules were combined together to form a larger blend. The combined granules were then blended with excipients to produce a formulation containing 75 wt % sodium ibuprofen dihydrate. This formulation was then converted into tablet form on a rotary press. It was observed that no punch coating occurred when the blend was pressed into tablets on the rotary press. It was also observed that no punch coating occurred when granules from Example 5 were formulated and pressed into tablets on the rotary press.

The composition of the formulation used in producing the tablets (sometimes hereinafter designated Formulation DTH) is 75% of sodium ibuprofen dihydrate, 21.37% of microcrystalline cellulose (MCC PH102; FMC Corporation), 1.96% PVP K-90 (Plasdone K-90, International Specialty Products Inc., Wayne, N.J.), 1.57% anhydrous sodium carbonate, and 0.10% colloidal silica (Aerosil 200; Evonik Industries, formerly Degussa Corporation). The tablet formulation is prepared by blending the granules with the microcrystalline cellulose and colloidal silica. For every 100 parts by weight of granules used for the DTH preparation, 21.21 parts by weight of microcrystalline cellulose and 0.127 parts by weight of colloidal silica are incorporated.

To prepare Formulation DTH, the following procedure is recommended: de-lump the granules and microcrystalline cellulose by sieving them separately through a 16-mesh screen. Weigh all three ingredients separately, prepare a preblend of colloidal silica and microcrystalline cellulose by mixing the colloidal silica and a portion of microcrystalline cellulose, pass this mixture through a 20-mesh sieve. Discharge the granules, the remaining microcrystalline cellulose, and the preblend into a low shear blender and blend for 10 minutes.

It is to be understood that Formulation DTH, while constituting a preferred formulation of this invention, should not be construed as limiting this invention to this particular formulation. For example, good results can be achieved by eliminating the sodium croscarmellose component from Formulation DTH. Other formulations utilizing the granules of this invention based on this disclosure may now occur to those of ordinary skill in the art.

Differential scanning calorimetry (DSC) scans of most of the granule samples produced in Examples 3-10 indicated the occurrence of an exothermal reaction just before a major solid state transition peaking around 100° C. The exothermal transition disappeared after holding the granules at elevated temperature (50° C.) conditions for a short time period. The position of the transition and the disappearance of the anomaly after holding granules under elevated temperature conditions indicated that the exothermal peak was related to stress in the granules.

Examples 11-20 involve experimental work conducted in order to determine what causes the stress and how to eliminate the stress, which appeared to be related to drying conditions. In addition to studying drying conditions, blending time in the wet granulation process was generally increased from 10 to 16 minutes. The experiments were conducted at batch sizes of 0.5 kg.

EXAMPLES 11-20

The procedures used in Examples 11-20 involved wet granulation of the components, drying of the granules, and analysis of the granules. In the granulation, operations of all Examples except Example 20, samples from the same specific lot of sodium ibuprofen dihydrate were used. In Example 20, the sodium ibuprofen dihydrate was a composite mixture of products from small bench scale crystallizations of sodium ibuprofen dihydrate recovered from an ibuprofen product sodium stream. This latter bench scale sodium ibuprofen dihydrate had a particle size several times greater than that of the lot of sodium ibuprofen dihydrate used in Examples 11-19. The granulation processing steps used involved (i) discharging sodium ibuprofen dihydrate (Na IBU) into the granulator bowl of the high shear granulator, (ii) de-lumping Na IBU, (iii) adding povidone solution to promote granulation under high shear, (iv) adding anhydrous sodium carbonate powder into the blend and resume blending, and (v) transferring granules to a fluidized bed dryer for drying. Only in Example 12 was a de-lumping step used. In Example 12, before addition of PVP solution, sodium ibuprofen dihydrate was de-lumped for 90 seconds by operating the chopper at 2500 RPM and at an impeller speed of 300 RPM. At the end of de-lumping, PVP solution was poured into the granulator and the chopper and impeller speed were maintained at the same rates for set periods of time. Then, the speeds were reduced to enable granulation at reduced shear. Afterwards, the granulator was stopped and the lid was removed. Sodium carbonate (<20 mesh) was then sprinkled on the blend. The lid was placed back and blended for about 5 minutes at 2500 RPM chopper and 300 RPM impeller speed and another 5 minutes at 1000 RPM chopper and 150 RPM impeller speeds. Table 8 summarizes the operation parameters for the high-shear granulation, for the de-lumping operation, and for the addition of the polyvinylpyrrolidone (PVP) solution. In Table 8, "CPR" again designates "chopper" and "IMP" designates "impeller".

TABLE 8

WET GRANULATION PROCESS - DE-LUMPING DURING & AFTER ADDITION OF PVP SOLUTION

| | De-lumping | | | PVP solution during addition and after addition | | | | | |
| --- | --- | --- | --- | --- | --- | --- | --- | --- | --- |
| Ex. No. | CPR RPM | IMP RPM | Time sec | CPR RPM | IMP RPM | Time sec | CPR RPM | IMP RPM | Time sec |
| 11 | — | — | — | 2500 | 300 | 90 | 1000 | 150 | 210 |
| 12 | 2500 | 300 | 90 | 2500 | 300 | 200 | 1000 | 150 | 300 |
| 13 | — | — | — | 2500 | 300 | 200 | 1000 | 150 | 300 |
| 14 | — | — | — | 2500 | 300 | 300 | 1000 | 150 | 300 |
| 15 | — | — | — | 2500 | 300 | 300 | 1000 | 150 | 300 |
| 16 | — | — | — | 2500 | 300 | 300 | 1000 | 150 | 300 |
| 17 | — | — | — | 2500 | 300 | 300 | 1000 | 150 | 300 |
| 18 | — | — | — | 2500 | 300 | 300 | 1000 | 150 | 300 |
| 19 | — | — | — | 2500 | 300 | 300 | 1000 | 150 | 300 |
| 20 | — | — | — | 2500 | 300 | 300 | 1000 | 150 | 300 |

Table 9 summarizes the operating conditions used in the wet granulation process after adding the powdery anhydrous sodium carbonate to the contents in the granulator. In this way, the wet granulation procedure was completed. In Table 9, "CPR" again designates "chopper" and "IMP" designates "impeller". The term "n/a" designates "not applicable".

TABLE 9

OPERATION CONDITIONS AFTER
SODIUM CARBONATE ADDITION

| | After sodium carbonate addition | | | | | Holding Time |
|---|---|---|---|---|---|---|
| Trial | CPR RPM | IMP RPM | Time sec | CPR RPM | IMP RPM | Time sec | before Drying, minutes |
| 11 | 2500 | 300 | 90 | 1000 | 150 | 210 | n/a |
| 12 | 2500 | 300 | 300 | 1000 | 150 | 300 | n/a |
| 13 | 2500 | 300 | 300 | 1000 | 150 | 300 | n/a |
| 14 | 2500 | 300 | 120 | 1000 | 150 | 240 | 30 |
| 15 | 2500 | 300 | 120 | 1000 | 150 | 240 | n/a |
| 16 | 2500 | 300 | 120 | 1000 | 150 | 240 | n/a |
| 17 | 2500 | 300 | 120 | 1000 | 150 | 240 | n/a |
| 18 | 2500 | 300 | 120 | 1000 | 150 | 240 | n/a |
| 19 | 2500 | 300 | 120 | 1000 | 150 | 240 | n/a |
| 20 | 2500 | 300 | 90 | 1000 | 150 | 210 | n/a |

At the end of the granulator operations, all of the wet granules were pneumatically transferred immediately to a fluidized bed dryer except for Example 14. In Example 14, the wet granules were kept in the granulator for 30 minutes before they were pneumatically transferred to the fluidized bed dryer for drying. The use of such holding time was for the purpose of determining whether stress in the wet granules may be released by allowing them to stand for a period of time prior to drying.

Table 10 outlines drying parameters used in this study. The base case for drying was use of an inlet air temperature of 70° C. with a product temperature of 40° C. as a control for moisture content as determined by weight loss at 110° C. Examples 11, 12, 13, 14, and 20 were conducted with inlet temperature set at 70° C., and the drying operations were terminated once product temperature reached 40° C. Example 15 was performed with inlet temperature set at 70° C., however samplings were carried out when product temperature reached 35, 40, 45 and 48° C. Instead of using product temperature as a control, Examples 16 and 17 used drying time as the control. In Example 16, at an inlet temperature of 70° C., the first sample for analysis was collected when product temperature reached 40° C., and the drying was continued at the same inlet temperature with additional samples being collected after additional 10 and 30 minutes of drying, respectively. In Example 17, at an inlet temperature of 70° C., the first sample was collected when product temperature reached 40° C. At this point, the inlet temperature was reduced to 60° C. and additional samples were collected after additional drying periods of 20 and 60 minutes, respectively. Example 18 employed an inlet temperature of 80° C. and Example 19 used an inlet temperature of 60° C. Table 10 provides a summary of these operations.

TABLE 10

FLUID BED DRYING CONDITIONS AND SAMPLING POINTS
The samples from these operations were then subjected to the following analyses:

| Ex. No. | Inlet temp | | Sampling Point Based on Product Temperature | | | | Sampling Point Based on Drying Time, Minutes | | |
|---|---|---|---|---|---|---|---|---|---|
| 11 | 70° C. | 40° C. | — | — | — | — | — | — | — |
| 12 | 70° C. | 40° C. | — | — | — | — | — | — | — |
| 13 | 70° C. | 40° C. | — | — | — | — | — | — | — |
| 14 | 70° C. | 40° C. | — | — | — | — | — | — | — |
| 15 | 70° C. | 35° C. | 40° C. | 45° C. | 48° C. | — | — | — | — |
| 16 | 70° C. | 40° C. | — | — | — | 70° C. | 10 | 30 |
| 17 | 70° C. | 40° C. | — | — | — | 60° C. | 20 | 60 |
| 18 | 80° C. | 40° C. | — | — | — | — | — | — | — |
| 19 | 60° C. | 40° C. | — | — | — | — | — | — | — |

DSC Phase Transition and Moisture Content

Table 11 provides differential scanning calorimeter data and moisture content, as determined by moisture balance of granules collected under varying fluid bed drying conditions. The data show that about all granules with a moisture content of 13.0% or greater have a heat of transition >170 joule/gram. It is also clear that over drying may lead to lower heat of phase transition. Nevertheless, overdried samples that provide DSC thermal treatment curves which peak in the range of about 100° C. to about 102° C., and which the size of the DSC peak, which peak corresponds to solids-to-solids phase transition, is at least about 150 joules per gram, will give satisfactory results when utilized in forming solid dosage forms.

TABLE 11

DIFFERENTIAL SCANNING CALORIMETRY AND
MOISTURE WEIGHT LOSS OF GRANULES AT 110° C.

| Example Number & Further Sample Identification where Applicable | Location of Phase Transition | | Heat of Transition Joule/g | Weight Loss at 110° C., wt. % Wt. % |
|---|---|---|---|---|
| | initial, ° C. | peak, ° C. | | |
| 11 | 98.9 | 100.7 | 173.1 | 13.16 |
| 12 | 98.5 | 100.6 | 173.1 | 13.30 |
| 13 | 98.6 | 100.7 | 173.3 | 13.37 |
| 14 | 98.7 | 100.5 | 175.1 | 13.36 |
| 15-35° C. | 98.7 | 100.7 | 172.9 | 13.49 |
| 15-40° C. | 98.6 | 100.5 | 174.9 | 13.45 |
| 15-45° C. | 98.7 | 100.6 | 168.9 | 11.96 |
| 15-48° C. | 98.0 | 101.4 | 147.7 | 9.31* |
| 16-70° C. - 0 min | 98.8 | 100.7 | 177.0 | 13.03 |
| 16-70° C. - 10 min | 98.8 | 100.9 | 166.2 | 11.48 |
| 16-70° C. - 30 min | 97.7 | 101.7 | 144.1 | 7.33* |
| 17-60° C. - 0 min | 98.7 | 100.8 | 178.0 | 13.11 |
| 17-60° C. - 20 min | 98.1 | 101.7 | 159.3 | 11.01 |
| 17-60° C. - 60 min | 97.8 | 101.1 | 130.0 | 5.46* |
| 18 | 98.7 | 100.6 | 172.9 | 12.99 |
| 19 | 98.8 | 100.6 | 167.6 | 12.12 |
| 20 | 98.4 | 100.9 | 173.3 | 13.06 |

*This sample is deemed overdried and thus is not a preferred sample; however, it exhibited desirable DSC thermal characteristics and thus may be used in preparing solid dosage forms.

Particle Size Distributions

Particle size distributions of granules show that all granules have narrow size distributions with the exception of Example 20, which as prepared from a composite sodium ibuprofen dihydrate crystallized from ibuprofen product sodium stream (PSS). The average mean particle size for granules generated from the sodium ibuprofen dihydrate lot used in Examples 11-19 was 172 microns with a standard deviation of 12 microns. The mean particle size of the composite sodium ibuprofen dihydrate used in Example 20 was 324 microns and the granule prepared had a mean particle size of 232 microns.

The similarity of the mean particle size and size distribution of the granules from Examples 11 through 19 indicates that the process is very robust, as regards particle size distribution. The differences of mean size and size distribution as between Examples 11-19 and Example 20 suggests that particle size of granules is a function of the particle size of the starting sodium ibuprofen dihydrate.

Sieve Analyses and Assay Content in Varying Sieve Size Fractions

Twenty grams of granules from Example 12 and 18 were placed on a stack of 12-inch diameter sieves consisting 20, 30, 40, 60, 80, 100, and 200 mesh stainless steel sieves. After shaking for 20 minutes, granules retained on each sieve were weighed and the retained granules of selected size fractions were submitted for HPLC assay determination. The assay contents expressed as wt % of theoretical are given in Table 12 below. The data show that about 90 wt % of the particles are in the 40-200 mesh range and generally lager particle size corresponds to higher assay content. It also shows that the difference in assay content for majority of the particles (40-200 mesh range) is negligible.

TABLE 12

GRANULE SIEVE RETENTIONS AND ASSAY CONTENTS

| Source of | Sieve Retention, wt % | | Assay, wt % of Theoretical | |
|---|---|---|---|---|
| Granule | Example 12 | Example 18 | Example 12 | Example 18 |
| 20 mesh | 2.0 | 2.0 | 79 | 77 |
| 30 mesh | 0.5 | 0.5 | | |
| 40 mesh | 0.5 | 0.5 | | |
| 60 mesh | 11.8 | 17.2 | 93 | 97 |
| 80 mesh | 25.0 | 28.9 | 97 | 98 |
| 200 mesh | 52.0 | 43.6 | | |
| Pan (<200 mesh) | 8.3 | 7.4 | 102 | 102 |

In order to demonstrate the advantages of utilizing granules produced pursuant to this invention, granules produced in Example 11, 12, 13, 18, 19, and 20 were blended individually with other excipients to produce a formulation, in this case Formulation DTH, for use in forming tablets. The individual Formulation DTH blends were then sequentially fed into a 10-station rotary press (Minipress II; GlobePharma, Inc., New Brunswick, N.J.) to prepare tablets containing about 600 mg of ibuprofen equivalent of the sodium salt. The main compression was kept at about 10 kilonewton (KN), pre-compression was kept at about 1.5 KN and the production rate was kept in the range of 100-120 tablets per minute. Tablet samples were collected throughout the runs. At least one set of tablet sample of about 30 tablets was collected for each blend. A total of 12 tablet sample sets were collected from the seven Formulation DTH blends processed through the tablet preparation process.

Dissolution of the tablets shows an average theoretical dissolution of 59% at 10 minutes, 98% dissolution at 20 minutes and 13.9 minutes at 80% dissolution. The dissolution rates of Formulation DTH tablets tested were significantly better than regulatory dissolution rates.

Average friability for 100 drops was 0.14 wt % for all 12 sets of tablets collected.

Figure 8:
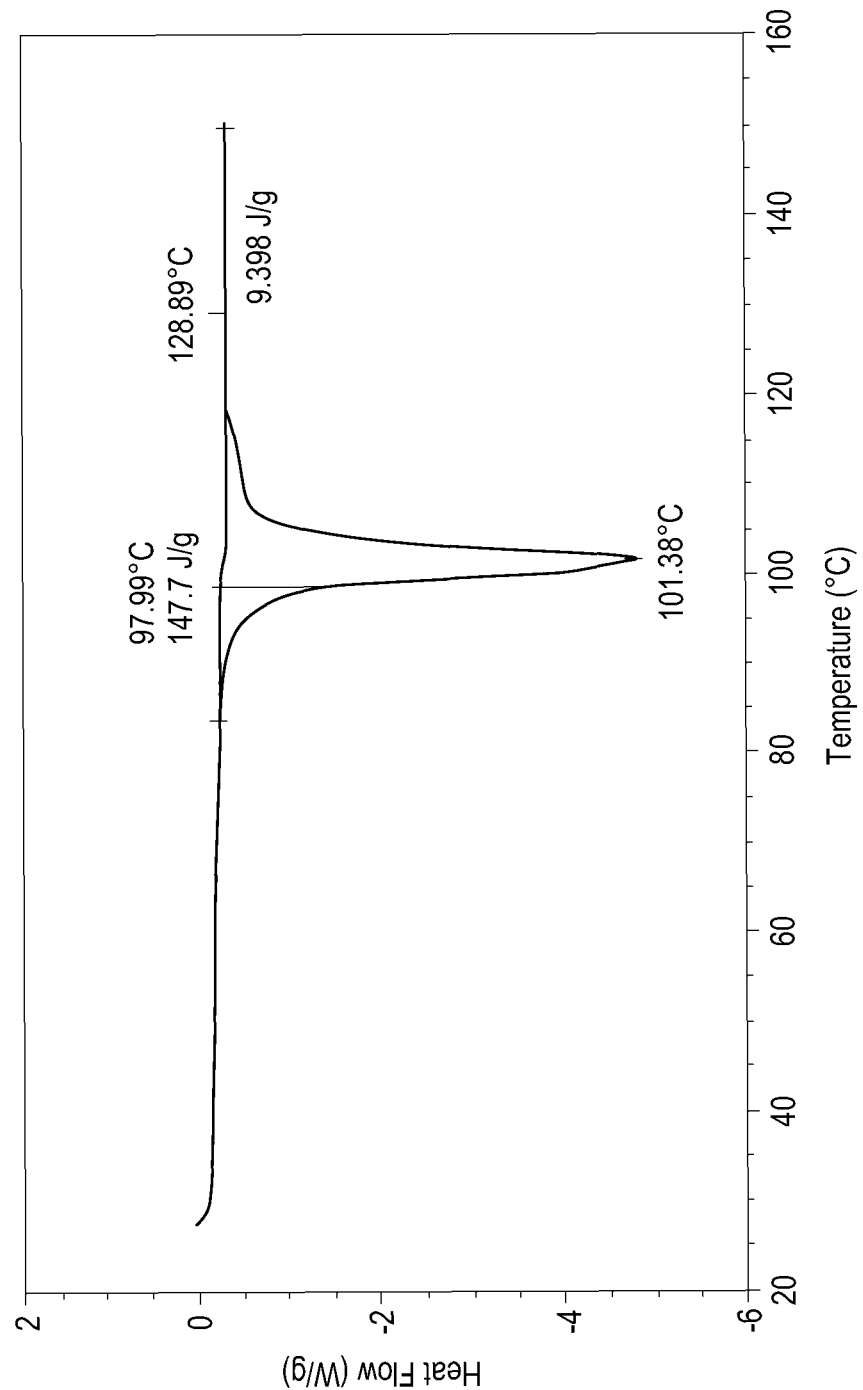
FIG. 8 is a differential scanning calorimetry curve of granules of this invention produced in Example 15 sampled with a drier inlet temperature set at 70° C., and when the drying temperature of the granules reached 48° C.
Figure 9:
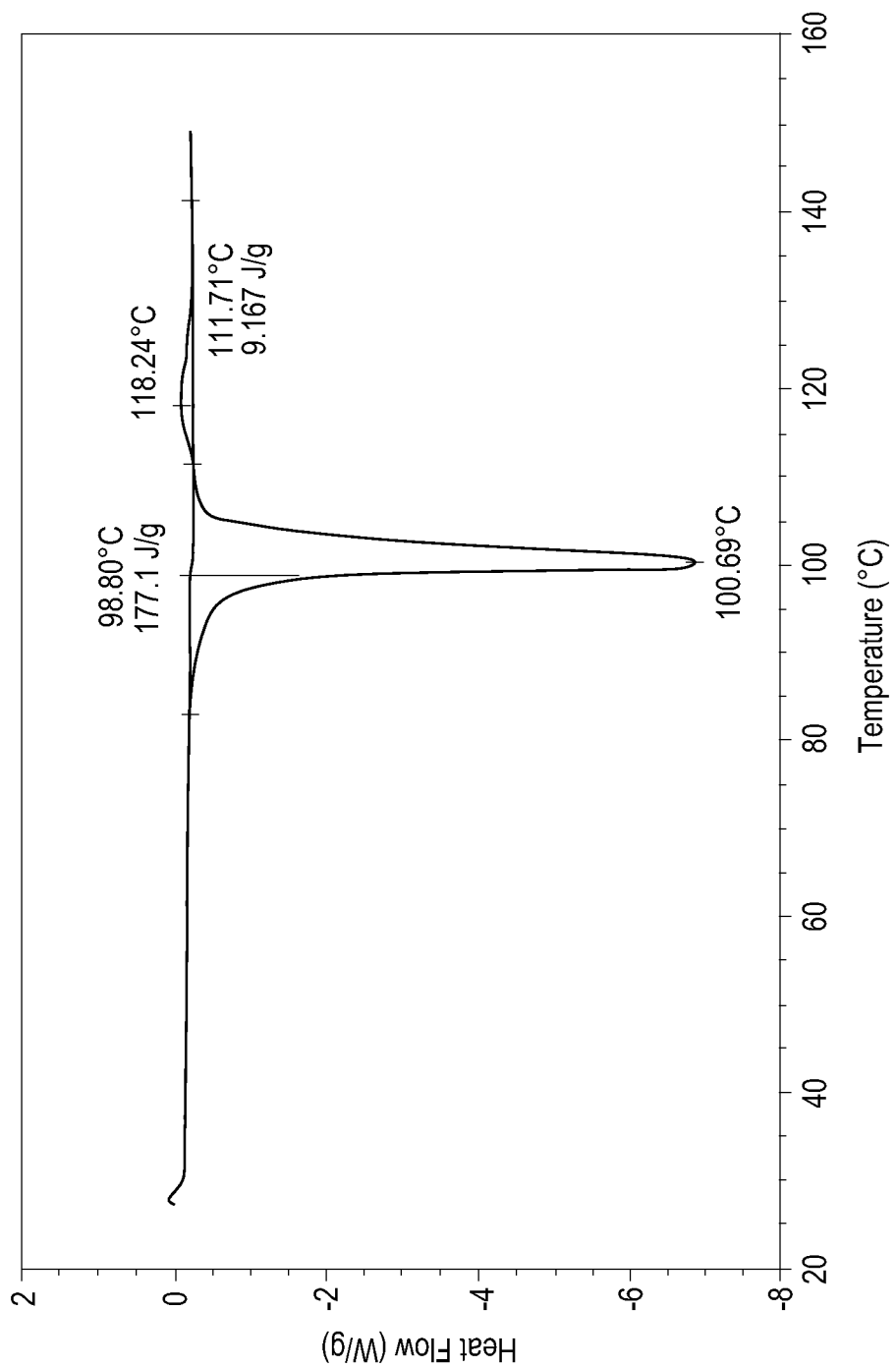
FIG. 9 is a differential scanning calorimetry curve of granules of this invention produced in Example 16 sampled with a drier inlet temperature set at 70° C., and when the drying temperature of the granules reached 40° C.
Figure 10:
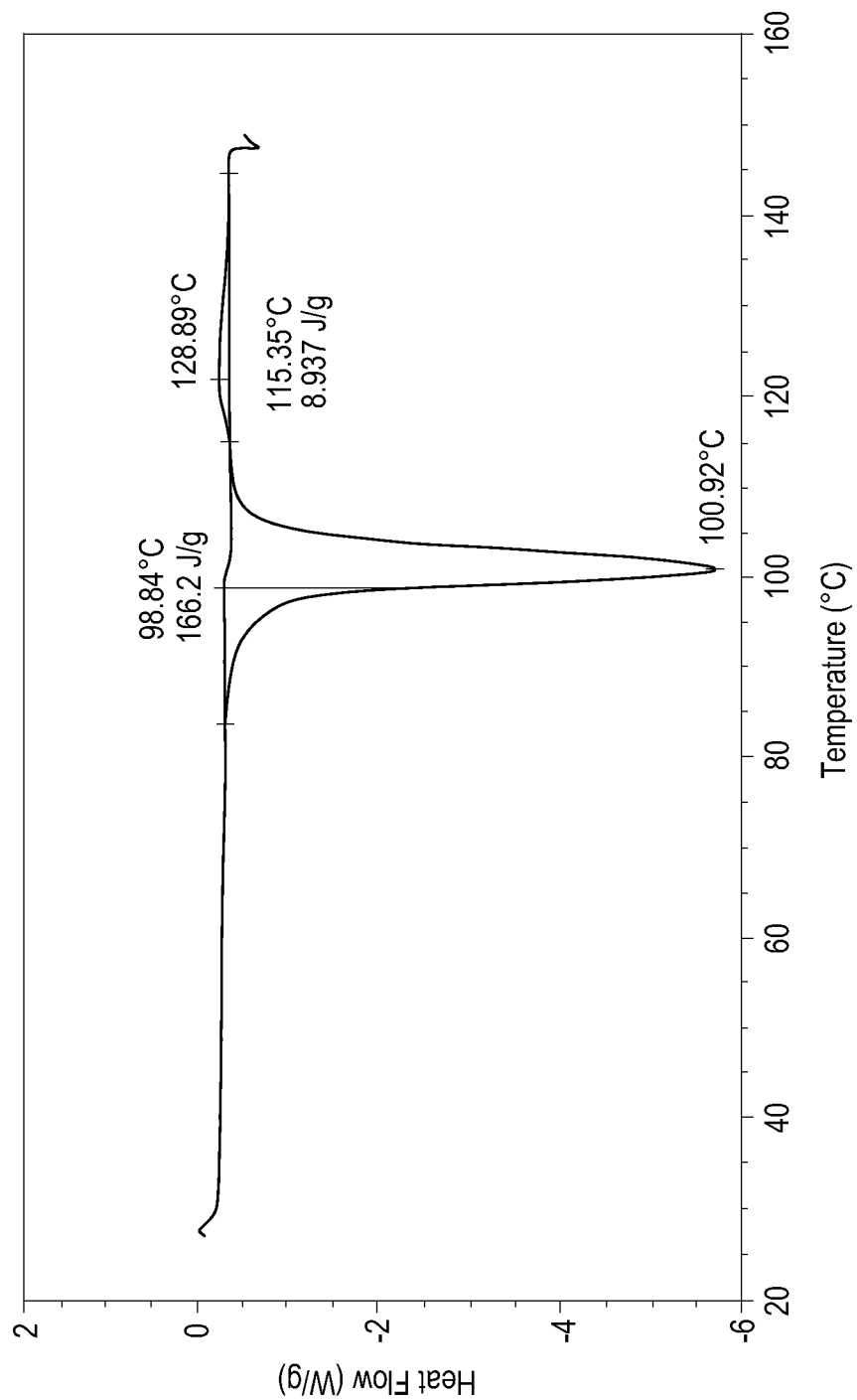
FIG. 10 is a differential scanning calorimetry curve of granules of this invention produced in Example 16 with a drier inlet temperature set at 70° C., and sampled 10 minutes after the sample of FIG. 10 were taken.
Figure 11:
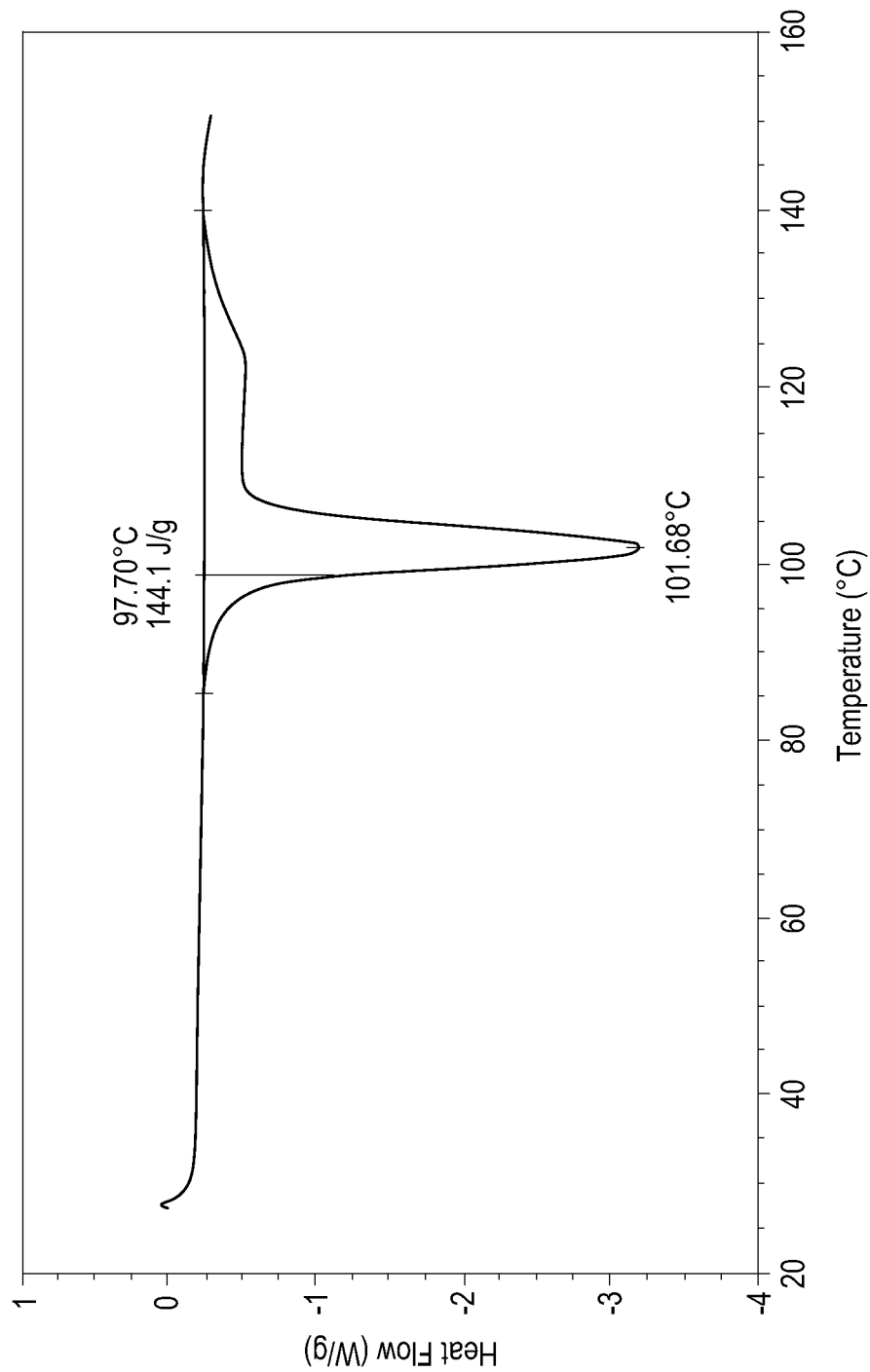
FIG. 11 is a differential scanning calorimetry curve of granules of this invention produced in Example 16 with a dryer inlet temperature set at 70° C., and sampled 30 minutes after the sample of FIG. 10 was taken.
Figure 12:
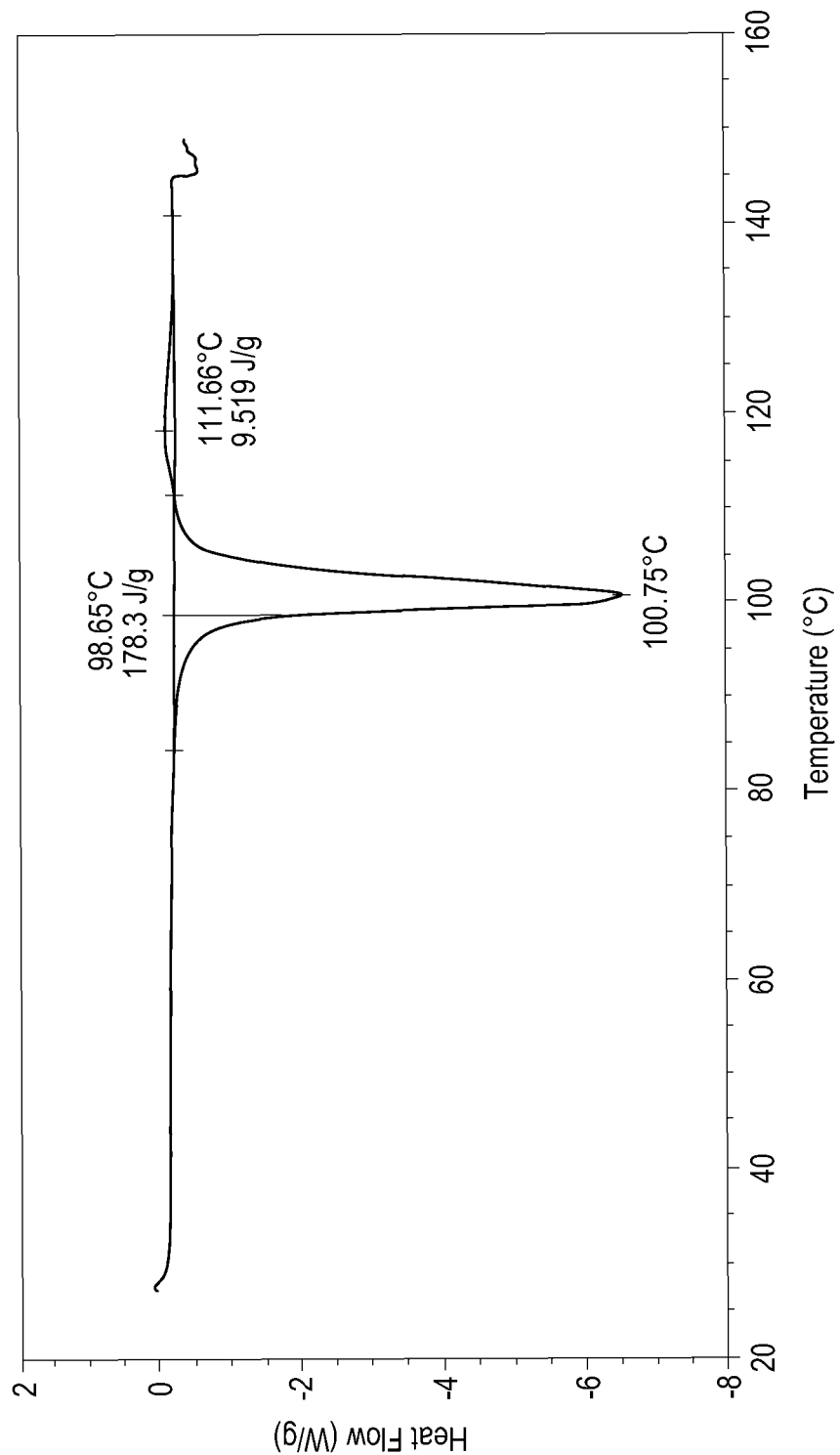
FIG. 12 is a differential scanning calorimetry curve of granules of this invention produced in Example 17 with a dryer inlet temperature set at 70° C., and sampled when the granules reached a temperature of 60° C.
Figure 13:
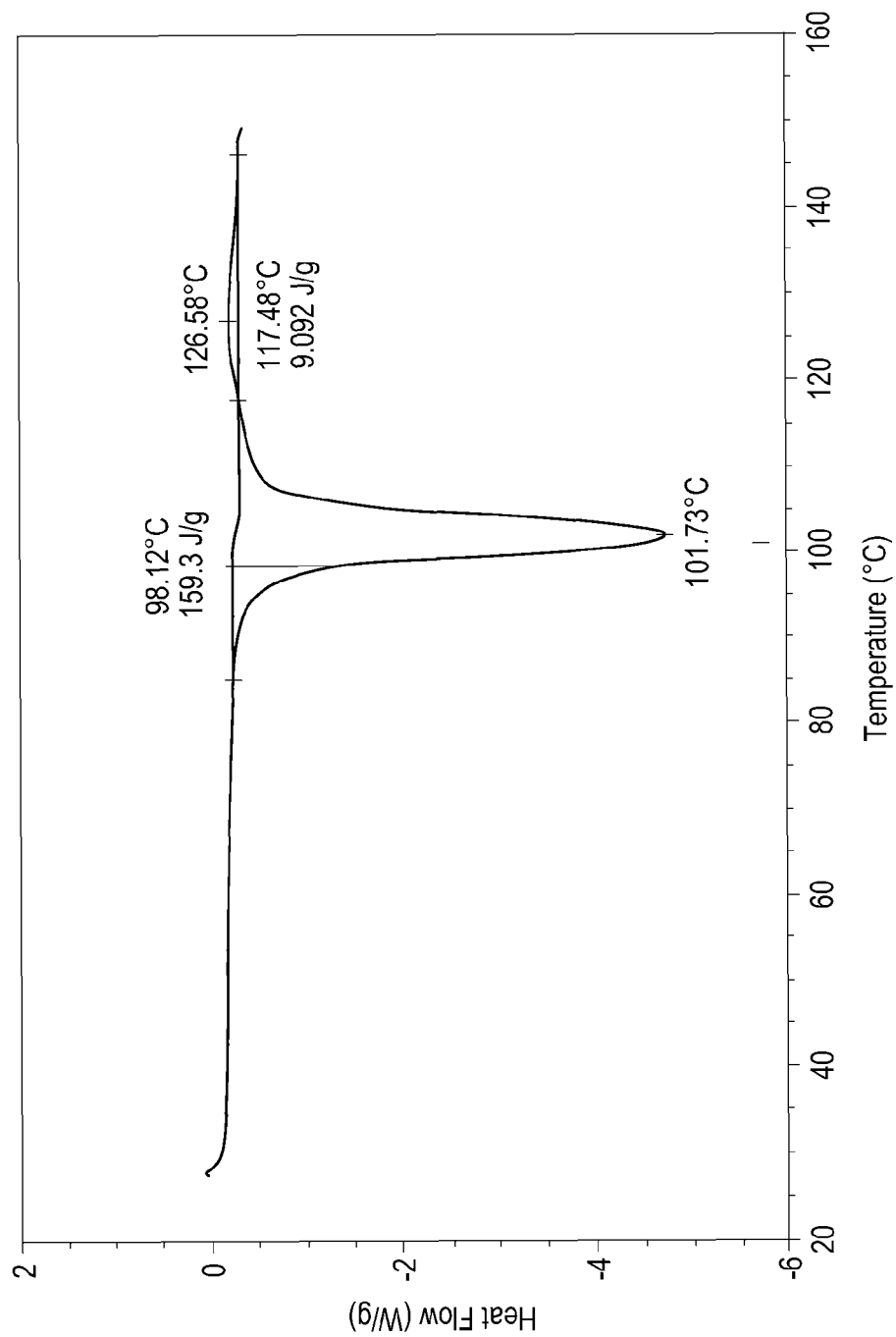
FIG. 13 is a differential scanning calorimetry curve of granules of this invention produced in Example 17 by reducing the dryer inlet air temperature from 70 to 60° C., and sampled when the granules were at a temperature of 60° C. for 20 minutes.
Figure 14:
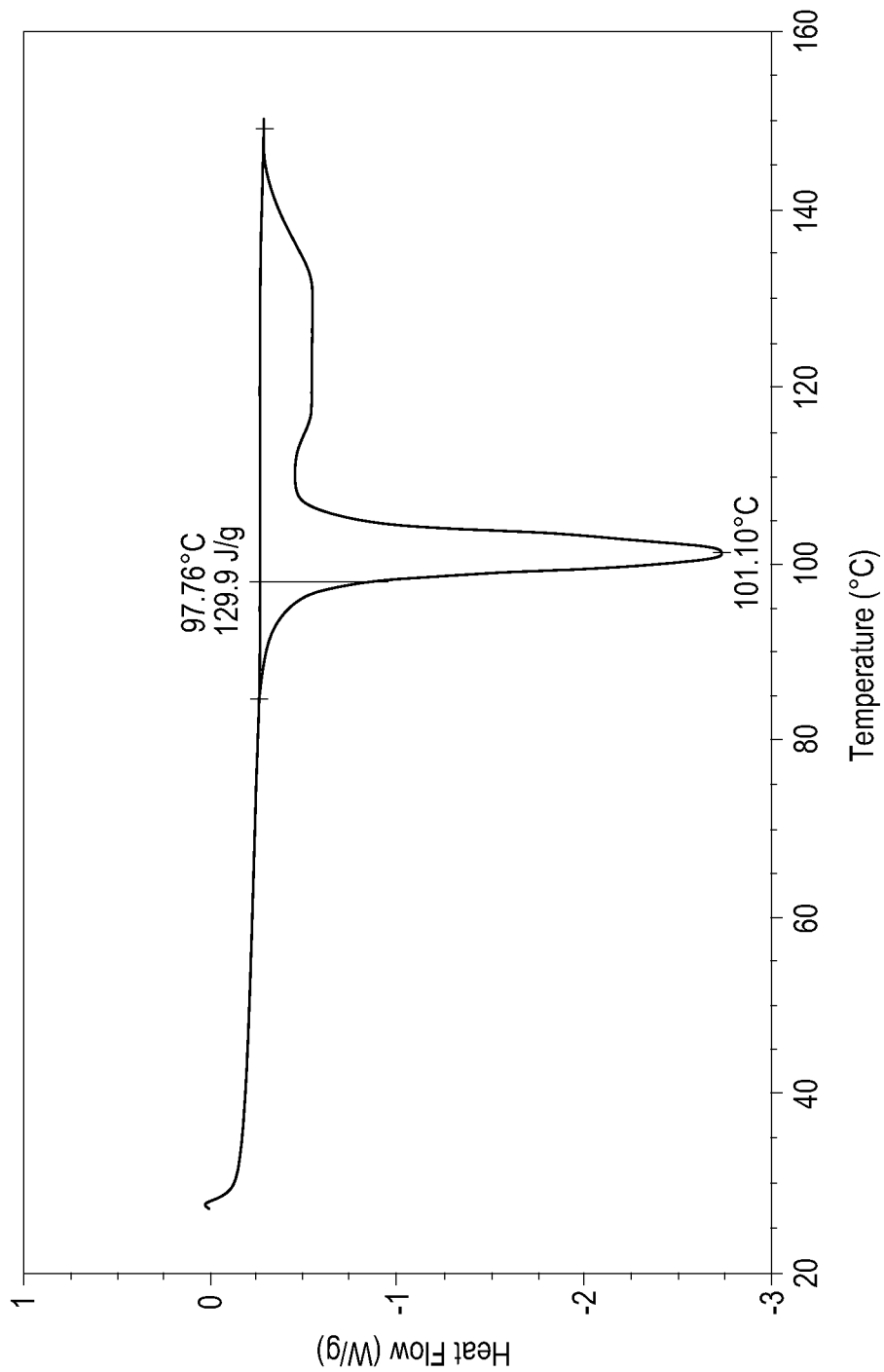
FIG. 14 is a differential scanning calorimetry curve of granules of this invention produced in Example 17 by reducing the dryer inlet air temperature from 70 to 60° C., and sampled when the granules were at a temperature of 60° C. for 60 minutes.
Figure 15:
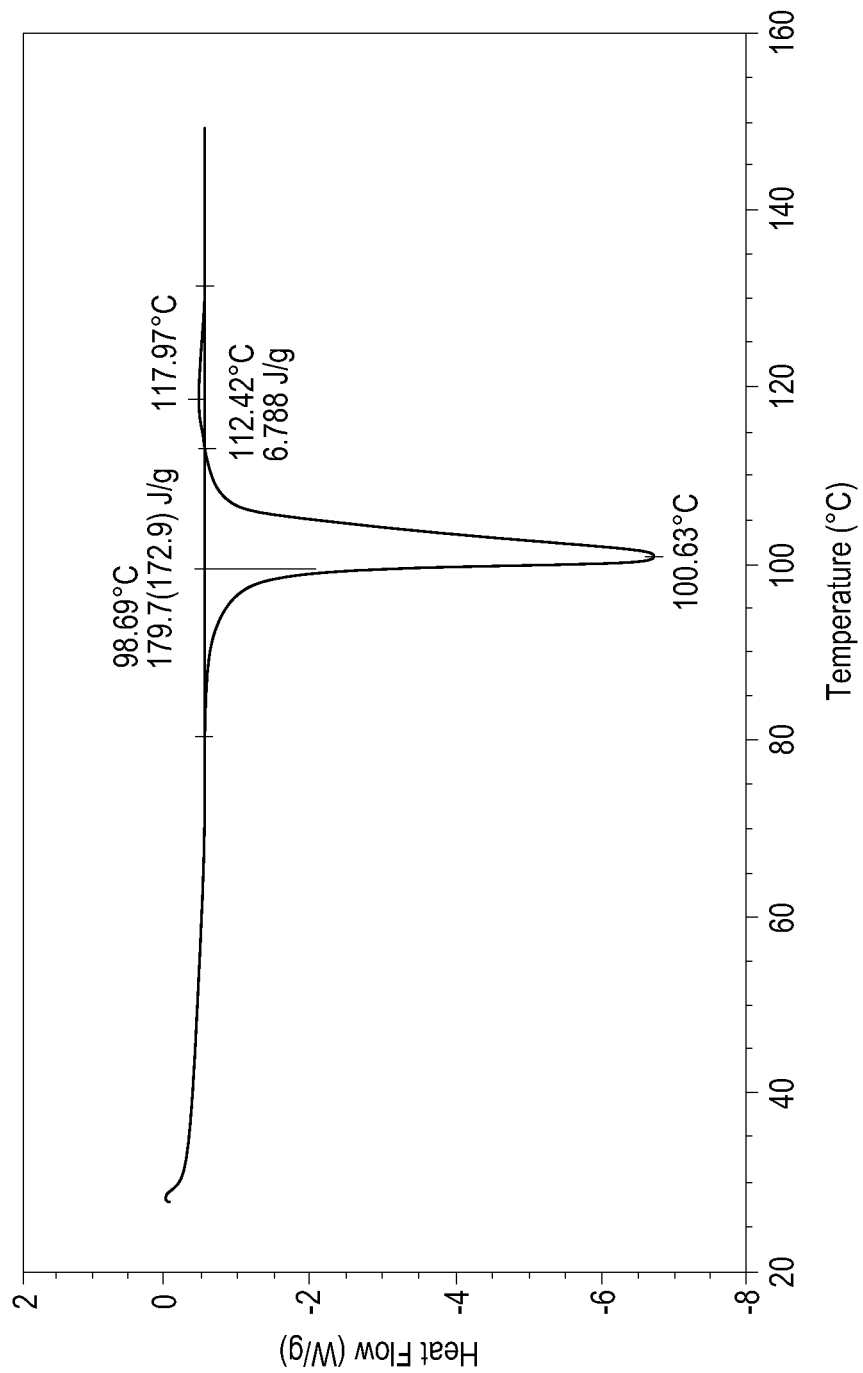
FIG. 15 is a differential scanning calorimetry curve of the granules of this invention produced in Example 18.
Figure 16:
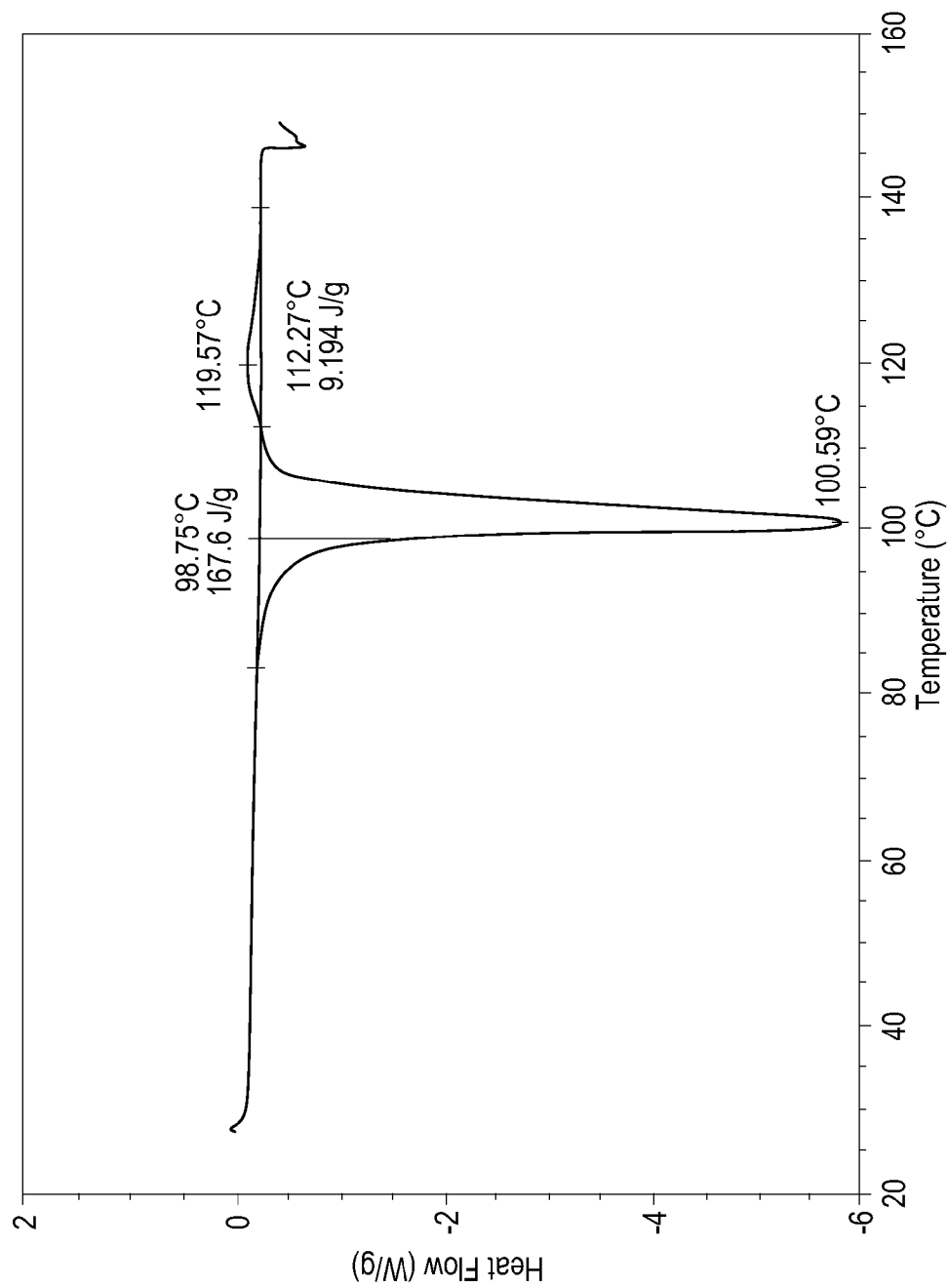
FIG. 16 is a differential scanning calorimetry curve of the granules of this invention produced in Example 19.
Figure 17:
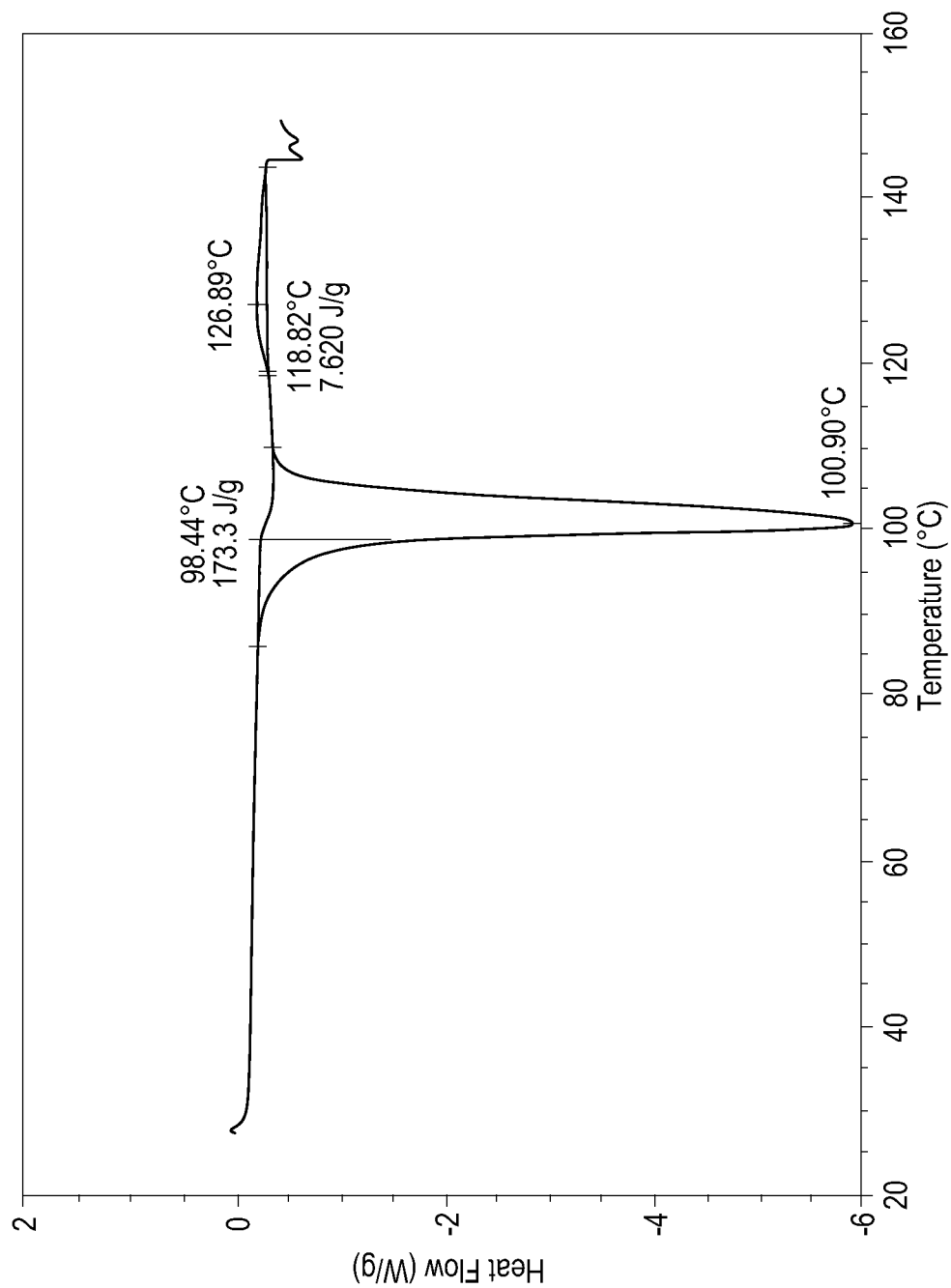
FIG. 17 is a differential scanning calorimetry curve of the granules of this invention produced in Example 20.

Referring now to the drawings, FIGS. 1-17 are differential scanning calorimetry curves of granules of this invention produced in Examples 11 through 20 and as discussed in relation to Table 11 and summarized under the Brief Description of the Drawings. As noted in connection with that Table, the samples of FIGS. 8, 11, and 14 were deemed usable but are not preferred because of having been over-dried during the drying step.

The composition of one type of preferred granules of this invention and the composition of one type of preferred formulation for producing tablets of this invention are described in Table 13. Batch sizes and compositions of such preferred granules and of a preferred tablet formulation of this invention are described in Table 14.

TABLE 13

FORMULATIONS OF GRANULES AND DTH BLEND

| | Wet Granules | Dry Granules | | Formulation DTH |
|---|---|---|---|---|
| Na ibu dihydrate | 85.95% | 95.50% | | 75.00% |
| G2.5P2A | — | — | 78.53% | |
| PVP K90 | 2.25% | 2.50% | | 1.96% |
| Na2CO3 | 1.80% | 2.00% | | 1.57% |
| MCC PH 102 | — | — | 16.37% | 16.37% |
| Na Croscarmellose | — | — | 5.00% | 5.00% |
| Colloidal Silica | — | — | 0.10% | 0.10% |
| Purified Water | 10.00% | | | |
| Total | 100.00% | 100.00% | 100.00% | 100.00% |

TABLE 14

BATCH SIZES AND COMPOSITIONS OF GRANULES AND DTH BLEND

| | Formulation of Granules | Formulation of DTH Blend |
|---|---|---|
| Batch size, dry, kg | 40.00 | 50.93 |
| Sodium Ibuprofen Dihydrate, kg | 38.20 | — |
| Granules, kg | — | 40.00 |
| Polyvinylpyrrolidone K-90, kg | 1.00 | — |
| Anhydrous Sodium Carbonate, kg | 0.80 | — |
| Mirocrystalline cellulose, kg | — | 8.34 |
| Sodium Croscarmellose, kg | — | 2.55 |
| Colloidal Silica, kg | — | 0.05 |
| Purified Water, kg | 4.44 | — |

A typical procedure for the preparation of one type of preferred granules of this invention at 40 kg dry batch size scale is as follows:
1. Initial Preparations
   a. Prepare a PVP stock solution (18.37 wt %) enough for several runs by dissolving polyvinylpyrrolidone (PVP K-90) in water using a high shear blender (3 kg in 13.33 kg purified water).
   b. Sieve sodium carbonate through a 20 mesh screen either by hand or using a mill equipped with a 20 mesh screen.
2. Granulation
   a. Weigh and charge 38.20 kg of sodium ibuprofen dihydrate into a high shear granulator.
   b. Weigh and charge 5.44 kg of the PVP solution to the granulator which is operating under high shear. After 4 minutes, switch to low shear operation and continue operation for another 4 minutes.
   c. Weigh sieved anhydrous sodium carbonate (0.80 kg) and add to the granulator under high shear for 4 minutes followed by another 4 minutes under low shear.
   d. Pneumatically transport granules to a fluid bed dryer, keep granules gently fluidized, and start drying with inlet temperature set at 60° C.

3. Drying Procedure
   a. Set inlet temperature at 60° C., monitor bowl and outlet temperatures, sample dryer periodically and stop drying when product temperature reaches about 40° C.
   b. Determine moisture content (Karl Fischer or moisture balance at 110° C.) from samples collected with moisture content of 13.4 wt % as the target.
4. Particle Size Adjustment
   a. Pass the dry granules through a 16-mesh sieve to remove >16 mesh particles. Record the weight of >16 mesh material.
   b. Mill >16 mesh granule through a size reducer and add to the <16 mesh portion.
   c. Retain a few hundred grams for quality control and weigh the remaining <16 mesh product.
   d. If not used for preparing tablets, store the granules in fiber drums with polyethylene lining.
5. Analyses
   a. Particle distributions through sieving using 16, 20, 40, 60, 80, 100 and 200 mesh screens.
   b. Determine moisture content (Karl Fischer or moisture balance at 110° C.).

One type of preferred formulation of this invention is formed from the preferred granules made as just described above, and has the composition shown in Table 15 below.

TABLE 15

| Component | Amount |
| --- | --- |
| Na ibuprofen | 70 wt % |
| Sodium carbonate | 1.47 wt % |
| Plasdone K-90 | 1.83 wt % |
| MCC | 21.60 wt % |
| Crospovidone | 2.0 wt % |
| Starch 1500 | 2.0 wt % |
| Silica | 0.1 wt % |
| Stearic Acid | 1.00 wt % |

The above formulation also produced high quality tablets using a 10-station rotary press (Minipress II; GlobePharma, Inc., New Brunswick, N.J.) to prepare tablets containing about 400 mg of ibuprofen equivalent of the sodium salt. Dissolution of the tablets made from this formulation showed an average theoretical dissolution of over 80% at 20 minutes. This is far better than the regulatory requirement of 80% at 60 minutes. For these tablets, the average friability for 100 drops was 0.23 wt %.

A typical procedure for the preparation of one type of preferred tablets of this invention from a preferred tablet formulation of this invention (Formulation 75) is as follows:
1. Determine the required quantities of the three excipients (microcrystalline cellulose, sodium croscarmellose, and colloidal silica) by multiplying the amount of granules produced as above, available for blending to the appropriate conversion factor. For examples, if 40 kg of granules is to be blended for preparation of Formulation DTH, the microcrystalline cellulose (MCC) requirement is then 8.34 kg (40 kg×0.2084, the latter number being the conversion factor for MCC), the sodium croscarmellose requirement is 2.56 kg (40 kg×0.0637, the latter number being the conversion factor for sodium croscarmellose), and colloidal silica requirement is 0.051 kg (40 kg×0.00127, the latter number being the conversion factor for colloidal silica).
2. Sieve MCC and croscarmellose sodium separately through a 16-mesh screen and set aside the respective required weighed quantities of these two separate excipients. Set aside about 500 grams of the MCC in a plastic bag (e.g., using a bag of 2-5 liter size).
3. Weigh and add colloidal silica to the bag containing MCC, mix the bag contents, break up any lumps by hand, and screen the mixture through a 20-mesh screen.
4. Charge the granules, MCC, sodium croscarmellose and pre-blend into a twin-shell blender, and blend for 10 minutes under low shear.
5. Discharge the blend into a fiber drum with polyethylene liner and retain a 500 gram sample.
6. Analyses
   a. Particle distributions by sieving using a stack of sieves consisting of 16, 20, 40, 60, 80, 100 and 200 mesh screens.
   b. Moisture content (Karl Fischer or moisture balance at 110° C.).
   c. Flow characterizations (Flodex and flowability index).
7. Prepare tablets from Formulation DTH using a rotary press operated under conventional conditions.

Following are illustrative formulations of this invention suitable for preparation of solid dosage form.

Formulation AA) is a formulation which comprises:
   About 40 to about 100 wt % of a formulation formed from components which comprise a granule composition formed from components in powder form, which components comprise (i) 80 to 98 parts by weight of sodium ibuprofen dihydrate on a dry basis, (ii) 1 to 4 parts by weight of anhydrous sodium carbonate on a dry basis, and (iii) 1 to 15 parts by weight of non-crosslinked polyvinylpyrrolidone on a dry basis;
   0 to about 25 wt % of microcrystalline cellulose, calcium hydrogen phosphate, or both;
   0 to about 8 wt % of crospovidone or sodium croscarmellose;
   0 to about 0.5 wt % of colloidal silica;
   0 to about 10 wt % starch; and
   0 to about 2 wt % stearic acid, magnesium stearate, or both.

Formulation BB) is a formulation in which the amount of the granule composition is in the range of about 70 to about 100 wt %, the amount of microcrystalline cellulose is 0 to about 20 wt %, and the amount of crospovidone or sodium croscarmellose is 0 to about 8 wt %, and the amount of colloidal silica is about 0.05 to about 0.2 wt %.

Formulation CC) is a formulation in which the amount of the granule composition is in the range of about 75 to about 100 wt %, the amount of microcrystalline cellulose is 0 to about 20 wt %, and the amount of crospovidone or sodium croscarmellose is 0 to about 6 wt %, and the amount of colloidal silica is 0 to about 0.2 wt %.

Formulation DD) is a formulation in which the amount of the granule composition is in the range of about 60 to about 90 wt %, the amount of microcrystalline cellulose, calcium hydrogen phosphate dihydrate, or both, is about 10 to about 30 wt %, the amount of starch is 0 to about 6 wt %, the amount of crospovidone or sodium croscarmellose is 0 to about 6 wt %, the amount of colloidal silica is 0 to about 0.25 wt %, and the amount of stearic acid, magnesium stearate, or both, is 0 to about 2 wt %.

Formulation EE) is a formulation in which the amount of the granule composition is in the range of about 85 to about 100 wt %, the amount of microcrystalline cellulose, calcium hydrogen phosphate dihydrate, or both, is 0 to about 10 wt %, the amount of starch is 0 to about 6 wt %, the amount of crospovidone or sodium croscarmellose is 0 to about 5 wt %, the amount of colloidal silica is 0 to about 0.25 wt %, and the amount of stearic acid, magnesium stearate, or both, is 0 to about 2 wt %.

This invention also provides solid dosage form formed from a formulation of any of AA), BB), CC), DD), or EE). Also provided by this invention are dosage forms which comprise a hard-shell capsule containing a granule composition formed from components in powder form, which components comprise (i) 80 to 98 parts by weight of sodium ibuprofen dihydrate on a dry basis, (ii) 1 to 4 parts by weight of anhydrous sodium carbonate on a dry basis, and (iii) 1 to 15 parts by weight of non-crosslinked polyvinylpyrrolidone on a dry basis. In addition, this invention provides a method of preparing solid dosage forms of sodium ibuprofen dihydrate, which method comprises compressing in a rotary press a granule composition as described in the immediately preceding sentence.

In Examples 21-27, the following procedure was used in the preparation of granules from which the indicated tablets were punched.

The polyvinylpyrrolidone (Povidone K-90) was dissolved in water to form a solution prior to combining with other components (including sodium carbonate) in an effort to provide a uniform size distribution of the granules. The solution was then added to sodium ibuprofen in a V-blender equipped with a high shear intensifier bar (Maxi-Blend Lab V-Blender manufactured by GlobePharma, Inc.), and the granules were formed by operating the V-blender using high shear setting. The sodium carbonate powder is sieved and then added to the V-Blender, and allowed to mix. The wet granules are discharged from the V-Blender into a pan. The granules are placed in an oven and dried at 50° C. The water content of the granules was measured to be between 12.5 to 15 wt % as determinable by measurement of weight loss at 110° C. The material is then sieved to remove large granules.

The granules are then used to prepare a fully formulated blend for tablet preparation. The granules are dry blended using the V-blender. The sieved microcrystalline cellulose, sodium croscarmellose, and disintegrant of choice are allowed to mix for 10 minutes. The sieved fumed silica is then added to V-blender and allowed to blend for 5 minutes. Finally, the sieved lubricant of choice is added to the V-blender and allowed to mix for 5 minutes. The final drum-to-hopper composition had the composition as set forth in the tables.

EXAMPLE 21

Stearic acid and steel punch surfaces gave heavy sticking. The granule formulation in Table 16 was prepared by adding a lubricant (1 wt % Stearic acid) to the 75 wt % blend intended for drum to hopper applications (DTH). A function of a lubricant in a tablet formulation is to prevent sticking of the tablet to the punch faces, and to reduce friction between the die wall and the tablet during compression and ejection of the tablet. However, upon processing the formulation into 400 mg as active tablets in a 10-station rotary press having steel surface punches (GLOBEPHARMA 10-station rotary press equipped with transducers that measures pre-compression, main compression, ejection and RPM), heavy sticking was observed. An increase in the compression force did not clean the punches and sticking did not improve. The final blend was composed of 74.2 wt % of sodium ibuprofen dihydrate, 1.57 wt % sodium carbonate, 1.94 wt % polyvinylpyrrolidone, 4.95 wt % sodium croscarmellose, and 16.21% microcrystalline cellulose. The main compression force was 13.9 KN, the recompression force was 0.2 KN, the ejection force was 0.1 kilonewtons, and the press speed was 9 RPM.

Other ionic lubricants such as calcium stearate, magnesium stearate, and sodium lauryl sulfate were added in the same manner and proportions as stearic acid in Example 21. A high degree of sticking on the punch surfaces were observed and the characteristics of these tablets could not be examined.

Stearic acid and chrome plated punch surfaces gave no observable sticking. The granules formed in Example 1 were used to make 400 mg as active tablets using chrome-plated punches. The appearances of the tablets were acceptable. There were no visible imperfections on the surface of the tablets. There was no visible coating on the upper and lower punch faces. The chrome-plated punches reduced the sticking thereby greatly enhancing tablet appearance. The punch used was a GLOBEPHARMA 10-station rotary press equipped with transducers that measure pre-compression, main compression, ejection and RPM. The main compression force was 14.7 KN, the precompression force was 0.2 KN, the ejection force was 0.3 kilonewtons, and the press speed was 12 RPM.

TABLE 16

Drum-to-Hopper Composition (75 wt %) and Lubricant Stearic Acid

| 400 mg rounds Non-Chrome Plated Punches | Wt % |
|---|---|
| Na-Ibu (DTH-75) | |
| Sodium Ibuprofen | 74.20% |
| Sodium Carbonate | 1.57% |
| Povidone K-90 | 1.94% |
| Na-croscarmellose | 4.95% |
| Fumed Silica | 0.16% |
| Microcrystalline Cellulose | 16.21% |
| Total | 99.03% |
| Stearic Acid | 1.00% |
| Total | 100.03% |

EXAMPLE 22

Calcium stearate and conventional steel punches gave heavy sticking to punch surfaces. The granule formulation in Table 17 was made by adding a lubricant (1 wt % Calcium Stearate) to the DTH 75 wt % blend. The formulation is comprised of 74.40 wt % sodium ibuprofen, 1.49 wt % sodium carbonate, 1.86 wt % povidone K-90, 4.75 wt % sodium croscarmellose, 0.10 wt % fumed silica, 15.55 wt % microcrystalline cellulose, and 1 wt % calcium stearate. These granules were formed into 400 mg tablets using conventional steel tablet punches. The punch used was a GLOBEPHARMA 10-station rotary press equipped with transducers that measure pre-compression, main compression, ejection and RPM. The main compression force was 15.1 KN, the precompression force was 0.1 KN, the ejection force was 0.2 kilonewtons, and the press speed was 9 RPM.

The appearance of the tablets were unacceptable and a heavy coating on the punch surface was observed. There was sticking and picking around the embossing of the tablets.

TABLE 17

Drum-to-Hopper Composition (75 wt %) and Lubricant (Calcium Stearate)

| 400 mg rounds<br>Non-chrome plated punches | Wt % |
|---|---|
| Na-Ibu (DTH-75) | |
| Sodium Ibuprofen | 74.40% |
| Sodium Carbonate | 1.49% |
| Povidone K-90 | 1.86% |
| Na-croscarmellose | 4.75% |
| Fumed Silica | 0.10% |
| Microcrystalline Cellulose | 15.55% |
| Total | 98.15% |
| Calcium Stearate | 1.00% |
| Total | 99.15% |

EXAMPLE 23

Magnesium stearate and conventional steel punches gave heavy sticking to punch surfaces. The granule formulation in Table 18 was comprised of 74.20 wt % sodium ibuprofen, 1.57 wt % sodium carbonate, 1.94 wt % povidone K-90, 4.75 wt % sodium croscarmellose, 0.16 wt % fumed silica, 16.21 wt % microcrystalline cellulose, and 1 wt % magnesium stearate. The granules were formed into 400 mg as active tablets using conventional steel tablet punches. The punch used was a GLOBEPHARMA 10-station rotary press equipped with transducers that measure pre-compression, main compression, ejection and RPM. The main compression force was 14.7 KN, the precompression force was 0.1 KN, the ejection force was 0.1 kilonewtons, and the press speed was 13 RPM.

The appearance of the tablets was not up to market standards. A heavy coating was observed on the punch surface.

TABLE 18

Drum-to-Hopper Composition (75 wt %) and Lubricant (Magnesium Stearate)

| 400 mg rounds<br>Non-chrome plated punches | Wt % |
|---|---|
| Na-Ibu (DTH-75) | |
| Sodium Ibuprofen | 74.20% |
| Sodium Carbonate | 1.57% |
| Povidone K-90 | 1.94% |
| Na-croscarmellose | 4.95% |
| Fumed Silica | 0.16% |
| Microcrystalline Cellulose | 16.21% |
| Total | 99.03% |
| Magnesium Stearate | 1.00% |
| Total | 100.03% |

EXAMPLE 24

Stearic acid and conventional steel punches gave heavy sticking to punch surfaces. The formulation in Table 19 was made by granulating 74.20 wt % sodium ibuprofen, 1.57 wt % sodium carbonate, 1.94 wt % povidone K-90, 4.95 wt % sodium croscarmellose, 0.16 wt % fumed silica, 13.21 wt % microcrystalline cellulose, 1 wt % stearic acid, and 3 wt % talc. These granules were made into 400 mg tablets using conventional steel tablet punches. The punch used was a GLOBEPHARMA 10-station rotary press equipped with transducers that measure pre-compression, main compression, ejection and RPM. The main compression force was 15.6 KN, the precompression force was 0.2 KN, the ejection force was 0.1 kilonewtons, and the press speed was 14 RPM.

The appearance of the tablets was not up to market standards. A heavy coating was observed on the punch surface.

TABLE 19

Drum-to-Hopper Composition (75 wt %), Lubricant (Stearic Acid), and Glidant (3 wt % Talc)

| 400 mg rounds<br>Non-chrome plated punches | Wt % |
|---|---|
| Na-Ibu (DTH-75) | |
| Sodium Ibuprofen | 74.20% |
| Sodium Carbonate | 1.57% |
| Povidone K-90 | 1.94% |
| Na-croscarmellose | 4.95% |
| Fumed Silica | 0.16% |
| Microcrystalline Cellulose | 13.21% |
| Total | 99.03% |
| Stearic Acid | 1.00% |
| Talc | 3.00% |
| Total | 100.03% |

EXAMPLE 25

Sodium lauryl sulfate and conventional steel punches gave heavy sticking to punch surfaces. The formulation in Table 20 was made by adding a surfactant (1 wt % Sodium Lauryl Sulfate) to the DTH 75 wt % blend. This formulation was composed of 74.20 wt % sodium ibuprofen, 1.57 wt % sodium carbonate, 1.94 wt % povidone K-90, 4.95 wt % sodium croscarmellose, 0.16 wt % fumed silica, 16.21 wt % microcrystalline cellulose, and 1 wt % sodium lauryl sulfate. These granules were made into 400 mg as active tablets using conventional steel tablet punches. The punch used was a GLOBEPHARMA 10-station rotary press equipped with transducers that measure pre-compression, main compression, ejection and RPM. The main compression force was 16 KN, the precompression force was 0.4 KN, the ejection force was 0.1 kilonewtons, and the press speed was 8 RPM.

The appearance of the tablets was not up to market standards, exhibiting heavy capping. A heavy coating was observed on the punch surface.

TABLE 20

Drum-to-Hopper Composition (75 wt %), Lubricant (Sodium Lauryl Sulfate)

| 400 mg rounds<br>Non-Chrome Plated Punches | Wt % |
|---|---|
| Na-Ibu (DTH-75) | |
| Sodium Ibuprofen | 74.20% |
| Sodium Carbonate | 1.57% |
| Povidone K-90 | 1.94% |
| Na-croscarmellose | 4.95% |
| Fumed Silica | 0.16% |
| Microcrystalline Cellulose | 16.21% |
| Total | 99.03% |
| Sodium Lauryl Sulfate | 1.00% |
| Total | 100.03% |

EXAMPLE 26

Chrome plated punches were used to make 400 mg as active tablets using high active content (95.5 wt %) sodium ibuprofen granules See Table 21. The three components in this formulation include sodium ibuprofen dihydrate, sodium carbonate, and polyvinylpyrrolidone. The punch used was a GLOBEPHARMA 10-station rotary press equipped with transducers that measure pre-compression, main compression, ejection and RPM. The main compression force was 15.8 KN, the precompression force was 0.2 KN, the ejection force was 0.1 kilonewtons, and the press speed was 10 RPM. Even though a lubricant was not used, the appearances of the tablets were marketably acceptable. There were no visible imperfections on the surface of the tablets and they were very shiny and glossy-like in appearance. No coating was observed on the upper and lower punch faces. The use chrome-plated punches reduced the sticking thereby greatly enhancing tablet appearance of the high active content granules.

The granules above were formed into tablets using conventional steel tablet punches. No lubricant was used. The appearance of the tablets was not up to market standards, exhibiting heavy capping. A heavy coating was observed on the punch surface. The embossing of the tablet exhibited sticking and picking imperfections.

TABLE 21

Sodium Ibuprofen granules (95.5 wt %)

| 400 mg rounds Non-Chrome Plated Punches | Wt % |
|---|---|
| Sodium Ibuprofen | 95.50% |
| Sodium Carbonate | 2.00% |
| Povidone K-90 | 2.50% |

EXAMPLE 27

Chrome plate punches were used to make 400 mg as active tablets. The formulation in Table 22 was composed of 75 wt % sodium ibuprofen, 1.57 wt % sodium carbonate, 1.96 wt % povidone K-90, 16.37 wt % microcrystalline cellulose, 2 wt % crospovidone, 2 wt % starch 1500, 0.10 wt % fumed silica, and 1 wt % stearic acid. The punch used was a GLOBEPHARMA 10-station rotary press equipped with transducers that measure pre-compression, main compression, ejection and RPM. The main compression force was 13.8 KN, the precompression force was 0.2 KN, the ejection force was 0.1 kilonewtons, and the press speed was 13 RPM. The tablet appearance was excellent, with no visible imperfections.

Stearic acid and conventional steel punches gave heavy sticking to punch surfaces. The granules above were formed into 400 mg as active tablets using conventional steel tablet punches. The punch used was a GLOBEPHARMA 10-station rotary press equipped with transducers that measure pre-compression, main compression, ejection and RPM. The main compression force was 13.5 KN, the precompression force was 0.3 KN, the ejection force was 0.3 kilonewtons, and the press speed was 10 RPM. The appearance of the tablets was not up to market standards, exhibiting sticking on the upper surface of the tablet. A mild coating was observed on the punch surface.

TABLE 22

Sodium Ibuprofen granules (95.5 wt %) with the addition of sodium carbonate (1.57 wt %), povidone K-90 (1.96 wt %), microcrystalline cellulose (16.37 wt %), crospovidone (2 wt %), starch 1500 (2 wt %), fumed silica (0.10 wt %) and stearic acid (1 wt %)

| 400 mg rounds Chrome Plated/Non-Chrome Plated Punches | Wt % |
|---|---|
| Sodium Ibuprofen | 75.00% |
| Sodium Carbonate | 1.57% |
| Povidone K-90 | 1.96% |
| Microcrystalline Cellulose | 16.37% |
| Crospovidone | 2.00% |
| Starch 1500 | 2.00% |
| Fumed Silica | 0.10% |
| Stearic Acid | 1.00% |
| Total | 100.00% |

Components referred to by chemical name or formula anywhere in the specification or claims hereof, whether referred to in the singular or plural, are identified as they exist prior to coming into contact with another substance referred to by chemical name or chemical type (e.g., another component, a solvent, or etc.). It matters not what chemical changes, transformations and/or reactions, if any, take place in the resulting mixture or solution as such changes, transformations, and/or reactions are the natural result of bringing the specified components together under the conditions called for pursuant to this disclosure. Thus the components are identified as ingredients to be brought together in connection with performing a desired operation or in forming a desired composition. Also, even though the claims hereinafter may refer to substances, components and/or ingredients in the present tense ("comprises", "is", etc.), the reference is to the substance, component or ingredient as it existed at the time just before it was first contacted, blended or mixed with one or more other substances, components and/or ingredients in accordance with the present disclosure.

Except as may be expressly otherwise indicated, the article "a" or "an" if and as used herein is not intended to limit, and should not be construed as limiting, a claim to a single element to which the article refers. Rather, the article "a" or "an" if and as used herein is intended to cover one or more such elements, unless the text expressly indicates otherwise.

The invention may comprise, consist or consist essentially of the materials and/or procedures recited herein.

This invention is susceptible to considerable variation in its practice. Therefore the foregoing description is not intended to limit, and should not be construed as limiting, the invention to the particular exemplifications presented hereinabove.

The invention claimed is:

1. A process for forming tablets of sodium ibuprofen dihydrate, said process comprising forming tablets in a rotary tablet press comprising chrome contact surfaces, and punches having a punch speed, from granules of sodium ibuprofen dihydrate, the granules having been formed by a process comprising the steps of bringing together in a low shear, high shear or fluidized-bed granulator components comprised of (i) 80-90 parts by weight on a dry basis of sodium ibuprofen dihydrate, (ii) 1 to 4 parts by weight on a dry basis of sodium carbonate, (iii) 1 to 10 parts by weight on a dry basis of non-crosslinked polyvinylpyrrolidone, and (iv) 8 to 12 parts by weight of water based on the total weight of (i), (ii), (iii), and (iv) to form a wet mixture;

granulating said wet mixture by low shear, high shear or fluidized-bed granulation to form wet granules;

drying wet granules to form dried granules having a moisture content in the range of about 12.5 to 15 wt % as determinable by measurement of weight loss at 110° C.; and removing by sieving dried granules having a particle size greater than 16 mesh, said process of forming tablets in a press comprising a precompression force and a main compression force, wherein no punch coating occurs during the tablet-forming process.

2. A process as in claim 1 wherein the main compression force is in the range of 10 to 20 kilonewtons.

3. A process as in claim 2 wherein the main compression force is in the range of about 12 to about 16 kilonewtons.

4. A process as in claim 1 wherein the precompression force is in the range of about 0.8 to about 1.0 kilonewtons.

5. A process as in claim 1 wherein the contact surfaces of the punch are chrome-plated.

6. A process as in claim 1 wherein the contact surfaces of the punch are chrome.

7. A process as in claim 1 wherein the punch speed is in the range of about 5 to about 20 RPM.

8. A process as in claim 1 wherein the press comprises a 10-station rotary press comprising chrome contact surfaces.

9. A process as in claim 1, wherein the main compression force is in the range of about 12 to about 16 kilonewtons; the press comprises a 10-station rotary press comprising chrome or chrome-plated contact surfaces.

10. A process as in claim 1, wherein said granulating takes place in a high shear granulator.

11. A tablet formed by the process of claim 1.

12. A tablet formed by the process of claim 9, wherein the tablet is a standard 400 mg as active round tablet.

* * * * *

UNITED STATES PATENT AND TRADEMARK OFFICE
CERTIFICATE OF CORRECTION

PATENT NO. : 9,629,809 B2
APPLICATION NO. : 13/714768
DATED : April 25, 2017
INVENTOR(S) : Boudoin et al.

Page 1 of 1

It is certified that error appears in the above-identified patent and that said Letters Patent is hereby corrected as shown below:

On the Title Page

In item (72), delete "Llimatta" on the third line and insert --"Liimatta"--.

Signed and Sealed this
Nineteenth Day of December, 2017

Joseph Matal
*Performing the Functions and Duties of the*
*Under Secretary of Commerce for Intellectual Property and*
*Director of the United States Patent and Trademark Office*